United States Patent
Remmal et al.

(10) Patent No.: US 11,872,216 B2
(45) Date of Patent: Jan. 16, 2024

(54) PHARMACEUTICAL FORMULATION COMPRISING CINEOLE AND AMOXICILLIN

(71) Applicant: ADVANCED SCIENTIFIC DEVELOPEMENTS, Bouskoura (MA)

(72) Inventors: Adnane Remmal, Fes (MA); Ahmed Amine Akhmouch, Casablanca (MA)

(73) Assignee: ADVANCED SCIENTIFIC DEVELOPMENTS, Bouskoura (MA)

(*) Notice: Subject to any disclaimer, the term of this patent is extended or adjusted under 35 U.S.C. 154(b) by 0 days.

(21) Appl. No.: 16/306,262

(22) PCT Filed: Jun. 2, 2017

(86) PCT No.: PCT/MA2017/000014
§ 371 (c)(1),
(2) Date: Nov. 30, 2018

(87) PCT Pub. No.: WO2017/209588
PCT Pub. Date: Dec. 7, 2017

(65) Prior Publication Data
US 2019/0255024 A1 Aug. 22, 2019

(30) Foreign Application Priority Data

Jun. 2, 2016 (FR) ...................... 1655017
Jun. 2, 2016 (FR) ...................... 1655018
Jun. 2, 2016 (MA) ........................ 39084
Jun. 2, 2016 (MA) ........................ 39085

(51) Int. Cl.
| | |
|---|---|
| *A61K 31/43* | (2006.01) |
| *A61P 31/04* | (2006.01) |
| *A61K 9/00* | (2006.01) |
| *A61K 9/10* | (2006.01) |
| *A61K 9/14* | (2006.01) |
| *A61K 31/352* | (2006.01) |
| *A61K 31/424* | (2006.01) |
| *A61K 31/05* | (2006.01) |

(52) U.S. Cl.
CPC ............ *A61K 31/43* (2013.01); *A61K 9/0053* (2013.01); *A61K 9/0095* (2013.01); *A61K 9/10* (2013.01); *A61K 9/145* (2013.01); *A61K 9/146* (2013.01); *A61K 31/05* (2013.01); *A61K 31/352* (2013.01); *A61K 31/424* (2013.01); *A61P 31/04* (2018.01)

(58) Field of Classification Search
CPC ...... A61K 31/05; A61K 31/424; A61K 31/43; A61K 31/352; A61K 9/0053; A61K 9/0095; A61K 9/10; A61K 9/145; A61K 9/146; H04N 19/105; H04N 19/11; H04N 19/13; H04N 19/159; H04N 19/172; H04N 19/176; H04N 19/46; H04N 19/52; H04N 19/593; H04N 19/597; A61P 11/00; A61P 13/00; A61P 13/10; A61P 13/12; A61P 15/00; A61P 19/02; A61P 19/08; A61P 1/02; A61P 27/16; A61P 31/04; A61P 43/00
See application file for complete search history.

(56) References Cited

U.S. PATENT DOCUMENTS

| | | | |
|---|---|---|---|
| 8,852,648 | B2 | 10/2014 | Salamone et al. |
| 9,901,550 | B2 | 2/2018 | Chami |
| 10,143,663 | B2 | 12/2018 | Chami |
| 2008/0171709 | A1 | 7/2008 | Remmal |
| 2008/0171768 | A1 | 7/2008 | Remmal |
| 2008/0214518 | A1 | 9/2008 | Remmal |
| 2008/0214568 | A1 | 9/2008 | Remmal |
| 2011/0136883 | A1* | 6/2011 | Injac ............. A61K 9/2013 514/397 |
| 2011/0269731 | A1 | 11/2011 | Couvreur et al. |

FOREIGN PATENT DOCUMENTS

| | | |
|---|---|---|
| WO | WO 2010/049899 | 5/2010 |
| WO | WO 2016/041958 | 3/2016 |

OTHER PUBLICATIONS

Orhan et al. (Turk J Biol, vol. 35, pp. 251-258, 2011). (Year: 2011).*
Notification of Transmittal of the International Search Report and the Written Opinion of International Application No. PCT/MA2017/000014, dated Jan. 30, 2018, pp. 1-21.
Gradinaru, A. C. et al. "Interactions Between Cardamom Essential Oil and Conventional Antibiotics Against *Staphylococcus aureus* Clinical Isolates" *Farmacia*, 2014, pp. 1214-1222, vol. 62, No. 6.
Abd El-Kalek, H. H. et al. "Synergistic Effect of Certain Medicinal Plants and Amoxicillin Against Some Clinical Isolates of Methicillin-Resistant *Staphylococcus aureus* (MRSA)" *International Journal of Pharmaceutical Applications*, 2012, pp. 387-398, vol. 3, No. 3.

(Continued)

*Primary Examiner* — Kara R McMillian
(74) *Attorney, Agent, or Firm* — SALIWANCHIK, LLOYD & EISENSCHENK

(57) ABSTRACT

The present invention relates to a pharmaceutical formulation in powder form comprising amoxicillin, cineole and a pharmaceutically acceptable oil. The present formulation may also comprise clavulanic acid. It is intended for oral administration, preferably after suspension in an aqueous solvent. The present invention also relates to a combination of cineole and amoxicillin for use in the treatment of an infectious pathology, preferably a bacterial infection, in an individual. The present combination may also comprise a β-lactamase inhibitor, preferably clavulanic acid. The combination according to the invention makes it possible in particular to combat infections caused by bacteria that are resistant to antibiotics, preferably to antibiotics of the β-lactamine family.

14 Claims, 3 Drawing Sheets

(56) References Cited

OTHER PUBLICATIONS

Knezevic, P. et al. "Antimicrobial activity of *Eucalyptus camaldulensis* essential oils and their interactions with conventional antimicrobial agents against multi-drug resistant *Acinetobacter baumannii*" *Journal of Ethnopharmacology*, 2016, pp. 125-136, vol. 178.

Marinas, I. et al. "Rosmarinus officinalis essential oil as antibiotic potentiator against *Staphylococcus aureus*" *Biointerface Research in Applied Chemistry*, 2012, pp. 271-276, vol. 2, No. 1.

Craft, B. D. et al. Antioxidant Properties of Extracts Obtained from Raw, Dry-roasted, and Oil-roasted US Peanuts of Commercial Importance, Plant Foods for Human Nutrition, Mar. 3, 2010, pp. 311-318, vol. 65, No. 3.

Written Opinion in International Application No. PCT/MA2017/000014, dated Jan. 30, 2018, pp. 1-10.

Eze, F. I. et al. "Synthesis, Physicochemical Properties, and Antimicrobial Studies of Iron (III) Complexes of Ciprofloxacin, Cloxacillin, and Amoxicillin" *International Journal of Medicinal Chemistry*, 2014, Article ID 735602, pp. 1-6.

Gradinaru, A.-C. "Antimicrobial Activity of Native and Exotic Plant Species Against the Causative Agents of Lower Respiratory Tract Infections; Interactions With Conventional Antibiotics" *University of Medicine and Pharmacy*, PhD Thesis Abstract, 2014, pp. 1-10.

Shan-Ying, C. et al. "Chromatographic determination of high-molecular weight impurities in amoxicillin" *Journal of Pharmaceutical and Biomedical Analysis*, 2003, pp. 589-596, vol. 31.

Zayed, M.A. et al. "Synthesis and structure investigation of the antibiotic amoxicillin complexes of d-block elements" *Spectrochimica Acta Part A*, 2005, pp. 2231-2238, vol. 61.

\* cited by examiner

PHARMACEUTICAL FORMULATION COMPRISING CINEOLE AND AMOXICILLIN

CROSS-REFERENCE TO RELATED APPLICATION

This application is the U.S. national stage application of International Patent Application No. PCT/MA2017/000014, filed Jun. 2, 2017.

The present invention relates to the field of medicine, in particular that of bacterial infections. The invention relates to novel treatments and novel pharmaceutical formulations that are particularly suitable for medical or veterinary use in combatting bacterial infections, especially antibiotic-resistance infections.

TECHNICAL BACKGROUND OF THE INVENTION

Antibiotics are natural or synthetic substances which have bactericidal or bacteriostatic activity. Their generalized introduction after the Second World War was one of the most important therapeutic progresses of the XXth century. Antibiotic treatments have enhanced life expectancy by more than ten years, i.e. more than any other medical treatment. However, the generalized or even abusive use of certain antibiotics, including in preventive or curative treatment or as a food supplement in animal feed, in pisciculture, in veterinary and human medicine, or as pesticides for treating plants, has introduced a selection pressure which has led to the development of populations of antibiotic-resistant microorganisms and to a general reduction in therapeutic efficacy. In hospitals, this leads to an increased nosocomial risk, especially owing to the lack of a suitable treatment against certain multi-resistant germs.

In its latest report (April 2014) on the resistance of bacteria to antibiotics, the WHO points out "that unless the numerous actors concerned act urgently, in a coordinated manner, the world is heading toward a post-antibiotic era, where common infections and minor injuries that we have been able to treat for decades might once again kill". The resistance to certain "last-resort" treatments is already a reality. Thus, the resistance to treatments for potentially fatal infections caused by a common intestinal bacterium, *Klebsiella pneumoniae*, propagated throughout all regions of the world. The same is also true for resistance to one of the most widely used antibacterial medicaments in the treatment of urinary pathway infections caused by *E. coli*—fluoroquinolones. Recently, the failure of the last-resort treatment against gonorrhea—third-generation cephalosporins—has been confirmed in South Africa, Australia, Austria, Canada, France, Japan, Norway, United Kingdom, Slovenia and Sweden.

To confront this threat, the WHO is calling especially for the development of novel diagnostic products, novel antibiotics and other essential tools so that health professionals can maintain their advance on the progress of resistance.

Amoxicillin is a bactericidal β-lactamine antibiotic of the aminopenicillin family, which is indicated in the treatment of bacterial infections caused by sensitive germs. Amoxicillin is the antibiotic most commonly used, especially in children, since it has good oral absorption, a broad spectrum of antimicrobial action and a low cost. Amoxicillin is used in the treatment of various infectious diseases, especially those of the lungs, bronchae, nose, throat or ears, blood, digestive or urinary apparatus, genital pathways, gums and teeth.

Amoxicillin is often used in combination with another molecule, clavulanic acid, a β-lactamase inhibitor. β-Lactamase is an enzyme produced by bacteria that are resistant to β-lactamine antibiotics. By inhibiting β-lactamases, clavulanic acid prevents the inactivation of amoxicillin by the β-lactamases, and thus allows it to conserve its activity on the β-lactamase-producing resistant germs.

However, the appearance of particularly resistant bacterial germs, especially broad-spectrum ß-lactamase (BSBL) bacteria, which are no longer, or only partially, sensitive to the conventional ß-lactamase inhibitors such as clavulanic acid, has been witnessed in recent years.

Consequently, it is essential to find solutions for restoring the efficacy of amoxicillin against resistant bacteria, in particular bacteria which produce broad-spectrum β-lactamases (BSBL).

SUMMARY OF THE INVENTION

The inventors have discovered that cineole makes it possible to increase the efficacy of amoxicillin, in particular with respect to resistant bacteria. Specifically, they have demonstrated that the combination of amoxicillin and cineole makes it possible to obtain a synergistic effect which considerably reinforces the antibacterial activity of amoxicillin. They have thus developed a novel combination of molecules comprising amoxicillin, cineole and optionally clavulanic acid for efficiently combatting resistant bacterial germs, in particular germs which are resistant to the combination of amoxicillin and clavulanic acid.

The inventors have also developed a pharmaceutical formulation for considerably increasing the antibacterial activity of amoxicillin, alone or in combination with clavulanic acid, in particular with respect to bacterial germs that are resistant to the combination of amoxicillin and clavulanic acid.

Thus, the present invention relates, in a first aspect, to a pharmaceutical formulation in powder form comprising, or consisting essentially of, cineole, amoxicillin and a pharmaceutically acceptable oil.

Preferably, the formulation according to the invention also comprises a β-lactamase inhibitor, preferably clavulanic acid.

Preferably, the pharmaceutically acceptable oil of the formulation according to the invention is a vegetable, mineral, synthetic or animal oil, preferably a vegetable oil, and more preferably groundnut oil.

The formulation according to the invention may comprise between about 5 mg and about 100 mg of cineole per gram of powder, preferably between about 10 mg and about 50 mg of cineole per gram of powder, more preferably between about 20 mg and about 40 mg of cineole per gram of powder, and most particularly preferably about 33 mg of cineole per gram of powder.

The formulation according to the invention may also comprise between about 20 mg and about 500 mg of amoxicillin per gram of powder, preferably between about 50 mg and about 300 mg of amoxicillin per gram of powder, more preferably between about 150 mg and about 200 mg of amoxicillin per gram of powder, and most particularly preferably about 167 mg of amoxicillin per gram of powder.

The formulation according to the invention may also comprise between about 2 mg and about 50 mg of oil per gram of powder, preferably between about 10 mg and about 25 mg of oil per gram of powder, more preferably between about 15 mg and about 20 mg of oil per gram of powder, and most particularly preferably about 17 mg of oil per gram of powder.

The formulation according to the invention may finally comprise between about 1 mg and about 100 mg of β-lactamase inhibitor, preferably clavulanic acid, per gram of powder, preferably between about 5 mg and about 50 mg of β-lactamase inhibitor, preferably clavulanic acid, per gram of powder, more preferably between about 15 mg and about 25 mg of β-lactamase inhibitor, preferably clavulanic acid, per gram of powder, and most particularly preferably about 21 mg of β-lactamase inhibitor, preferably clavulanic acid, per gram of powder.

The formulation according to the invention may comprise in particular between about 5 mg and about 100 mg, preferably between about 10 mg and about 50 mg, of cineole per gram of powder; and/or between about 20 mg and about 500 mg, preferably between about 50 mg and about 300 mg, of amoxicillin per gram of powder; and/or between about 2 mg and about 50 mg, preferably between about 10 mg and about 25 mg, of oil per gram of powder; and/or optionally between about 1 mg and about 100 mg, preferably between about 5 mg and about 50 mg, of β-lactamase inhibitor, preferably clavulanic acid, per gram of powder.

Preferably, the formulation according to the invention comprises between about 20 mg and about 40 mg, preferably about 33 mg, of cineole per gram of powder; between about 150 mg and about 200 mg, preferably about 167 mg, of amoxicillin per gram of powder; between about 15 mg and about 20 mg, preferably about 17 mg, of oil per gram of powder; and/or optionally between about 15 mg and about 25 mg, preferably about 21 mg, of β-lactamase inhibitor, preferably clavulanic acid, per gram of powder.

The formulation according to the invention may have an amoxicillin/cineole mass ratio of between 2 and 8, preferably between 3 and 7, more particularly preferably between 4 and 6, and most particularly preferably an amoxicillin/cineole mass ratio of about 5.

The formulation according to the invention may have an amoxicillin/oil mass ratio of between 5 and 15, preferably between 7 and 13, more particularly preferably between 8 and 12, and most particularly preferably an amoxicillin/oil mass ratio of about 10.

The formulation according to the invention may have a cineole/oil mass ratio of between 0.1 and 5, preferably between 0.5 and 4, more particularly preferably between 1 and 3, and most particularly preferably a cineole/oil mass ratio of about 2.

The formulation according to the invention may have an amoxicillin/β-lactamase inhibitor mass ratio of between 5 and 11, preferably between 6 and 10, more particularly preferably between 7 and 9, and most particularly preferably an amoxicillin/β-lactamase inhibitor mass ratio of about 8.

The formulation according to the invention may be intended for oral administration, preferably after suspension in an aqueous solvent.

The formulation according to the invention may be packaged in a single-dose container, preferably a single-dose container containing between about 1 g and about 150 g of powder, more preferably between about 1 g and about 50 g of powder, preferably still between about 1 g and about 10 g of powder, and more particularly preferably about 3 g of powder.

The formulation according to the invention may also comprise at least one pharmaceutically acceptable excipient or support, preferably selected from the group consisting of a sweetener, a flavoring, an anticaking agent, a lubricant, a disintegrant, and a mixture thereof.

In a second aspect, the present invention also relates to the formulation as described above for use in the treatment of an infectious pathology in an individual, preferably an animal or a human.

Preferably, said infectious pathology is an infectious pathology of bacterial origin, more preferably an infectious pathology caused by a bacterium that is resistant to antibiotics of the β-lactamine family.

Preferably, the formulation is administered or intended to be administered to the individual over a period ranging from 1 day to 4 weeks and at a rate of from 3 to 30 grams per day, in one or more dosage intakes.

The present invention also relates, in a third aspect, to a process for manufacturing the pharmaceutical formulation according to the invention, comprising:
  the production of a wetting solution by mixing cineole and a pharmaceutically acceptable oil; and
  wetting of a powder comprising amoxicillin with the wetting solution so as to obtain a powdery preparation comprising amoxicillin, cineole and the oil.

Optionally, the process may also comprise the mixing of the powdery preparation comprising amoxicillin, cineole and the oil with a powder comprising a β-lactamase inhibitor, preferably clavulanic acid; and/or
  the addition of sweetener, flavoring and/or lubricant, and mixing thereof so as to obtain a homogeneous powder; and/or
  screening of the powder thus obtained; and/or
  packaging of the screened powder in single-dose containers.

Preferably, the powder comprising amoxicillin and/or the powder comprising a β-lactamase inhibitor, preferably clavulanic acid, also comprise a disintegrant and/or an anticaking agent.

In a fourth aspect, the present invention also relates to a molecular complex comprising more than two amoxicillin molecules organized linearly or in a ring and interacting with each other via noncovalent bonds.

Preferably, the molecular complex according to the invention is formed from at least three amoxicillin molecules, more preferably from three to six amoxicillin molecules, and most particularly preferably from four amoxicillin molecules.

The molecular complex according to the invention is obtained or may be obtained by dissolving amoxicillin in the presence of cineole in an aqueous solvent and in the absence of detergent.

The present invention relates, in a fifth aspect, to a therapeutic combination comprising, or consisting essentially of, cineole and amoxicillin for use in the treatment of a bacterial infection in an individual.

Preferably, the combination also comprises a β-lactamase inhibitor, preferably clavulanic acid.

In particular, the combination according to the invention may be a combined preparation for the simultaneous, separate or sequential use of cineole, amoxicillin, and optionally the β-lactamase inhibitor, preferably clavulanic acid.

Preferably, the bacterial infection is caused by a bacterium that is resistant to antibiotics, preferably to antibiotics of the β-lactamine family.

The treated individual is an animal, preferably a mammal, and most particularly preferably a human.

In the combination according to the invention,
  cineole may be administered or is intended to be administered to the individual at a dose of between about 0.1 mg/kg/day and about 50 mg/kg/day, preferably between about 0.5 mg/kg/day and about 20 mg/kg/day, and most particularly preferably between about 1 mg/kg/day and about 10 mg/kg of weight of the individual per day, and/or amoxicillin may be administered or is intended to be administered to the individual at a dose of between about 5 mg/kg/day and about 200 mg/kg/day, preferably between about 10 mg/kg/day and about 100 mg/kg/day, and most particularly preferably between about 15 mg/kg/day and about 50 mg/kg of weight of the individual per day, and/or the β-lactamase inhibitor, preferably clavulanic acid, may be administered or is intended to be administered to the individual at a dose of between about 0.1 mg/kg/day and about 50 mg/kg/day, preferably between about 0.5 mg/kg/day and about 20 mg/kg/day, and most particularly preferably between about 1 mg/kg/day and about 10 mg/kg of weight of the individual per day.

Preferably, the combination is administered or is intended to be administered to the individual over a period ranging from 1 day to 4 weeks, more preferably over a period of about 7 days, at a rate of only one or of several daily dosage intakes.

Preferably, cineole, amoxicillin and optionally the β-lactamase inhibitor, preferably clavulanic acid, of the combination are administered or are intended to be administered to the individual orally.

Amoxicillin and the β-lactamase inhibitor of the combination may be administered or may be intended to be administered to the individual simultaneously, preferably from a pharmaceutical composition comprising amoxicillin and the β-lactamase inhibitor.

Cineole, amoxicillin and optionally the β-lactamase inhibitor of the combination may be administered or may be intended to be administered simultaneously, preferably from a pharmaceutical composition comprising cineole, amoxicillin and optionally the β-lactamase inhibitor, or from a pharmaceutical composition comprising cineole and from a pharmaceutical composition comprising amoxicillin and optionally the β-lactamase inhibitor.

Preferably, cineole is administered or is intended to be administered sequentially or separately, preferably sequentially, relative to the amoxicillin and/or, optionally, to the β-lactamase inhibitor.

In a sixth aspect, the present invention also relates to a pharmaceutical composition comprising, or consisting essentially of, cineole, amoxicillin and a pharmaceutically acceptable excipient or support and optionally a β-lactamase inhibitor, preferably clavulanic acid.

The invention also relates, in a seventh aspect, to a kit for treating a bacterial infection in an individual, comprising:
(a) a pharmaceutical composition comprising, or consisting essentially of, cineole and a pharmaceutical composition comprising, or consisting essentially of, amoxicillin;
(b) a pharmaceutical composition comprising, or consisting essentially of, cineole and a pharmaceutical composition comprising, or consisting essentially of, amoxicillin and a β-lactamase inhibitor, preferably clavulanic acid;
(c) a pharmaceutical composition comprising, or consisting essentially of, amoxicillin and a pharmaceutical composition comprising, or consisting essentially of, cineole and a β-lactamase inhibitor, preferably clavulanic acid;
(d) a pharmaceutical composition comprising, or consisting essentially of, a β-lactamase inhibitor, preferably clavulanic acid and a pharmaceutical composition comprising, or consisting essentially of, cineole and amoxicillin; or
(e) a pharmaceutical composition comprising, or consisting essentially of, cineole, a pharmaceutical composition comprising, or consisting essentially of, amoxicillin, and a pharmaceutical composition comprising, or consisting essentially of, a β-lactamase inhibitor, preferably clavulanic acid; and
(f) optionally, a guide containing instructions for the use of such a kit.

The present invention also relates to a kit or a composition according to the invention for use in the treatment of a bacterial infection in an individual, preferably a bacterial infection caused by an antibiotic-resistant bacterium.

Preferably, the bacterial infection is selected from the group consisting of cystitis, in particular recurring acute cystitis, bacterial sinusitis, in particular acute maxillary sinusitis, otitis, in particular acute otitis media, bronchitis, in particular chronic and/or acute bronchitis, bronchopneumopathy, in particular chronic and/or acute bronchopneumopathy, pyelonephritis, upper genital tract infections, parodontitis, severe stomatological infections, in particular abscesses, phlegmons and cellulites, animal bites, bone and joint infections, in particular osteomyelitis; preferably said bacterial infection is a cystitis, in particular a cystitis caused by a bacterium that is resistant to antibiotics of the β-lactamine family.

Figure 4:
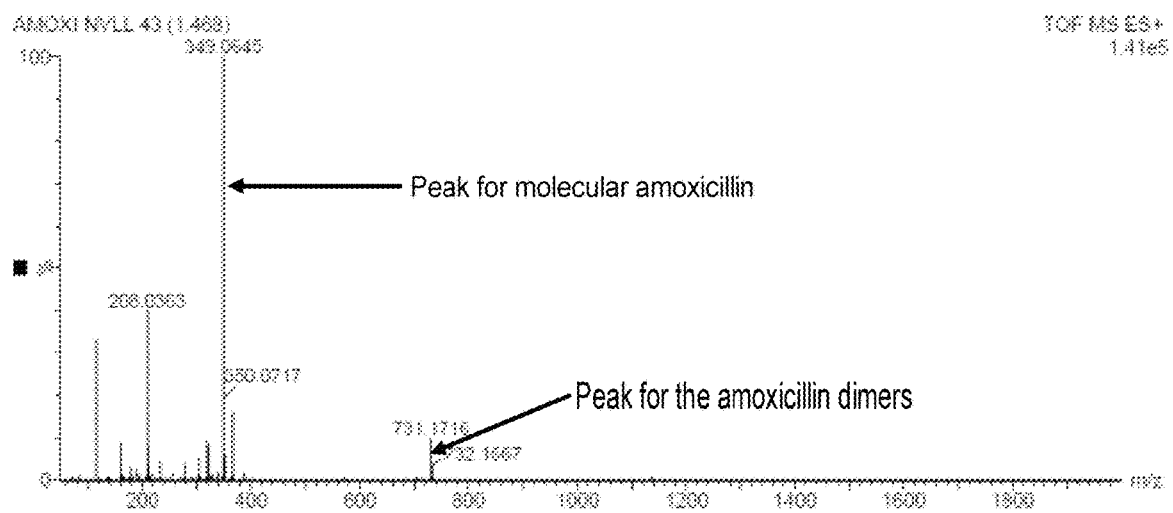
Figure 4:
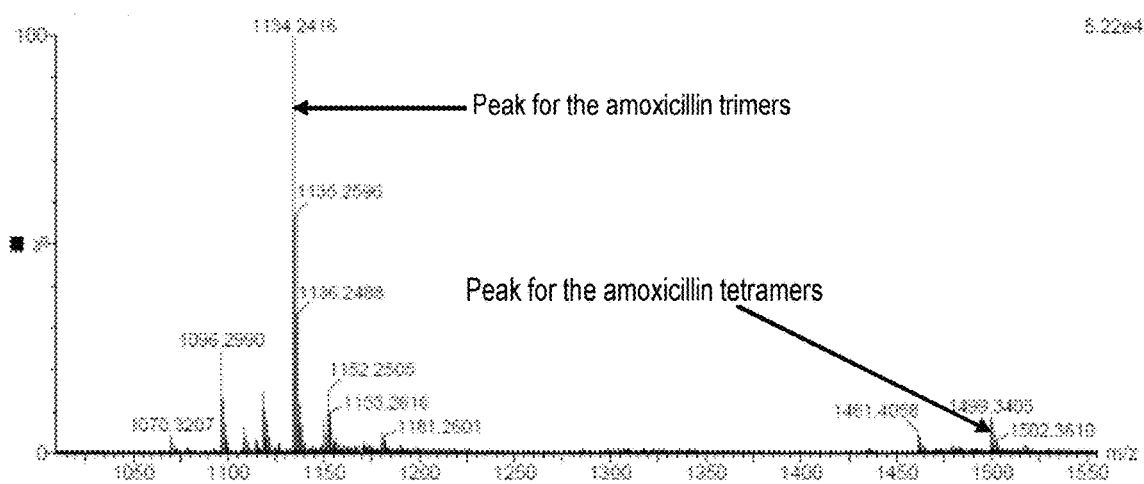

FIG. 4: Spectroscopic study of the formation of amoxicillin complexes. A (AMX alone): analysis by mass spectroscopy of amoxicillin alone in solution in water. B (AMX with cineole): analysis by mass spectroscopy of amoxicillin with cineole in solution in water.

DETAILED DESCRIPTION OF THE INVENTION

The inventors have demonstrated that the combination of amoxicillin with cineole makes it possible to obtain a synergistic effect which considerably increases the efficacy of amoxicillin, in particular with respect to resistant bacteria. They have in particular observed that cineole, at sub-therapeutic concentrations, protects amoxicillin from the inhibitory effect of β-lactamases, an enzyme produced by amoxicillin-resistant bacteria.

The inventors thus developed a novel therapeutic combination comprising amoxicillin, cineole and optionally clavulanic acid for efficiently combatting resistant bacterial germs, in particular germs which are resistant to the combination of amoxicillin and clavulanic acid.

The inventors also developed a pharmaceutical formulation in powder form combining cineole, amoxicillin and clavulanic acid. They observed that this combination makes it possible to considerably increase the antibacterial activity of amoxicillin and thus to efficiently treat patients suffering from infections with resistant germs.

This novel formulation also has excellent storage properties. In particular, the use of oil in the formulation makes it possible very efficiently to fix the cineole, which is a highly volatile agent, to the powdery support of this formulation. This makes it possible to propose a single formulation for the administration of active compounds which, after suspension in an aqueous solvent, can be readily administered orally. Having a single medicament, which in addition is administered orally, greatly increases the compliance with the treatments and thereby their efficacy.

The inventors also demonstrated that amoxicillin, in the presence of cineole, forms a complex of at least three amoxicillin molecules. The formation of this complex makes the amoxicillin molecules less accessible to β-lactamases and thus increases their therapeutic efficacy.

Thus, according to a first aspect, the present invention relates to a pharmaceutical formulation in powder form comprising, or consisting essentially, of cineole, amoxicillin and a pharmaceutically acceptable oil.

According to a second aspect, the present invention relates to a therapeutic combination comprising cineole and amoxicillin for use in the treatment of a bacterial infection in an individual. The combination according to the invention may also comprise a β-lactamase inhibitor, preferably clavulanic acid. In particular, the combination according to the invention may be a combined preparation for simultaneous, separate or sequential use of the active principles of the combination, preferably cineole, amoxicillin and clavulanic acid.

Definitions

In the present document, the term "about" refers to a range of values that are ±10% of the specified value. By way of example "about 50" comprises the values ±10% of 50, i.e. the values in the range 45 to 55. Preferably, the term "about" refers to a range of values that are ±5% of the specified value. It is understood that the values preceded by the term "about" should also be considered as specifically described in the present application.

The term "consists essentially of", as used herein, refers to a formulation according to the invention not comprising any active principle other than those mentioned in said formulation, in particular no other antibiotics or β-lactamase inhibitors.

As used herein, the term "pharmaceutically acceptable excipient or support" refers to any substance other than an active principle present in a pharmaceutical formulation. Its addition is especially intended to impart a particular consistency, or other particular physical or taste characteristics, to the final product, while at the same time avoiding any interaction, especially chemical interaction, with the active principle(s).

As used herein, the term "active principle" refers to a molecule which has a therapeutic effect. In particular, cineole, amoxicillin and β-lactamase inhibitors are active principles.

As used herein, the term "therapeutic effect" refers to an effect induced by an active principle, a composition according to the invention, or by a combination according to the invention, which is capable of preventing or retarding the appearance of a bacterial infection, or of curing or reducing the effects of a bacterial infection.

As used herein, the term "antibacterial effect" refers to an effect induced by an active principle, a composition according to the invention, or by a combination according to the invention, which is capable of reducing in an individual the amount and/or concentration of bacteria responsible for the bacterial infection.

As used herein, the term "synergistic effect" refers to a composition according to the invention or to a combination according to the invention which has a therapeutic effect and/or an antibacterial effect higher than that of the sum of the therapeutic effects and/or than that of the sum of the antibacterial effects of all the active principles present in said composition or in said combination, when they are taken individually. The presence of such an effect may be evaluated by calculating the fractional inhibitory concentration index (fic-index) as illustrated in example 1.

As used herein, the term "treatment" refers to any act directed toward improving the medical status of a person suffering from a bacterial infection. The treatment may be directed either toward improving the patient's condition, i.e. regression of the infection or of some of its symptoms, or toward eradication of the infection or of some of its symptoms. The treatment may also have an effect of preventing or slowing down the progress of a bacterial infection. The treatment may also have a prophylactic or preventive effect, i.e. preventing or retarding the appearance of the bacterial infection.

As used herein, the terms "amount" and "dose" are equivalent and may be used interchangeably.

As used herein, the term "therapeutically effective amount" refers to an amount of active principle, of composition according to the invention, or of combination according to the invention that is sufficient to induce a therapeutic effect. Alternatively, the term "therapeutically effective amount" may refer to an amount of active principle, of composition according to the invention, or of combination according to the invention that is sufficient to induce an antibacterial effect. It is obvious that the amount to be administered may be adapted by a person skilled in the art, as a function of the individual to be treated, the nature of the bacterial infection, etc. In particular, the doses and administration regimens depend on the nature, the stage of development and the severity of the bacterial infection to be treated, and also the weight, age and general state of health of the individual to be treated, or else on the judgment of the prescribing physician.

As used herein, the term "sub-therapeutic amount" refers to an amount of active principle that is insufficient alone to induce a therapeutic effect. Alternatively, the term "sub-therapeutic amount" may refer to an amount of active principle that is insufficient alone to induce an antibacterial effect.

As used herein, the terms "therapeutic combination" and "combined preparation" refer to a combination of active principles, preferably of cineole, amoxicillin and optionally clavulanic acid, which may each be formulated separately or as one or more formulations for simultaneous, separate or sequential administration, or a mixture of these modes of administration when the combination comprises more than two active principles.

As used herein, the term "simultaneous" refers to a combination according to the invention in which the active principles of the combination are used or administered simultaneously, i.e. at the same time.

As used herein, the term "sequential" refers to a combination according to the invention in which the active principles of the combination are used or administered sequentially, i.e. one after the other. Preferably, when the administration is sequential, all of the active principles are administered within an interval of not more than about 1 hour, preferably not more than about 10 minutes, and more preferably not more than about 1 minute.

As used herein, the term "separate" refers to a combination according to the invention in which the active principles of the combination are used or administered at separate times in the day. Preferably, when the administration is separate, the active principles are administered at intervals from about 1 hour to about 15 hours, preferably from about 1 hour to about 8 hours, and more preferably from about 1 hour to about 5 hours.

Cineole

As used herein, the term "cineole", "eucalyptol" or "1,8-cineole" refers to a cyclic ether (CAS No.: 470-82-6) belonging to the monoterpene group, i.e. terpenoids containing ten carbon atoms. Cineole is a natural, colorless organic compound which may be extracted especially from the essential oils of certain eucalyptus trees (for example *Eucalyptus polybractea*), from rosemary (for example *Rosmarinus officinalis*), from sagebrush (for example *Artemisia vulgaris*), but also from the essential oils of absinthe, of laurel, of sage, of basil and of camphor tree leaves (*Cinnamomum camphora*). Cineole may be used in any pharmaceutically acceptable form. As used herein, the term "pharmaceutically acceptable" refers to a molecule, to a compound or to a composition that is suitable for pharmaceutical administration. It is preferably used in a purified form. In its purified form, cineole is a liquid.

Amoxicillin

Amoxicillin (CAS No.: 26787-78-0) is a bactericidal β-lactamine antibiotic of the aminopenicillin family, which is indicated at the present time in the treatment of bacterial infections caused by sensitive germs. β-Lactamines are a broad class of antibiotics comprising penicillin derivatives, cephalosporins, monobactams and carbapenems. β-Lactamines are characterized by the presence of a β-lactam nucleus in their molecular structure, which gives them their bactericidal power.

In the formulation or the combination according to the invention, amoxicillin may be in any pharmaceutically acceptable form. Amoxicillin may thus be in the form of a pharmaceutically acceptable salt, in particular a sodium or potassium salt, in an anhydrous or hydrated form, preferably in the form of a trihydrate, or a mixture of these forms. In a preferred embodiment, the formulation or the combination according to the invention comprises amoxicillin trihydrate Pharmaceutically Acceptable Oil The pharmaceutical formulation according to the invention also comprises a pharmaceutically acceptable oil. As used herein, the term "oil" refers to a phase consisting of fatty substances that are liquid at room temperature and water-immiscible.

The oil used in the formulation according to the invention may be any pharmaceutically acceptable oil, i.e. any oil whose toxicological data are compatible with oral administration to an individual. The oil is preferably selected from the group consisting of animal, mineral, vegetable and synthetic oils and mixtures thereof.

Preferably, the oil used in the combination is not an essential oil. As used herein, the term "essential oil" refers to a concentrated and hydrophobic liquid of the volatile aromatic (odoriferous) compounds of a plant. The essential oil may be obtained by mechanical extraction, by cold pressing, with volatile solvents, with supercritical $CO_2$, by steam entrainment or dry distillation.

The oil may be used in the formulation according to the invention for its adsorbent properties. As used herein, the term "adsorbent" refers to an excipient that is capable of fixing liquid molecules, for example cineole molecules, to a solid support, for example a powdery support, in a pharmaceutical formulation.

In a particular embodiment, the formulation according to the invention comprises a mineral oil. The mineral oils are obtained by distillation of coal, of petroleum or of certain bituminous schists. Mineral oils especially comprise hydrocarbons, alkanes and paraffins. In particular, the mineral oil may be selected from the group consisting of refined paraffins, microcrystalline waxes, ozokerites, ceresins, petrolatum, and a mixture thereof.

In another particular embodiment, the formulation according to the invention comprises a synthetic oil. In particular, the synthetic oil may be selected from the group consisting of silicone oils, synthetic waxes, synthetic mono-, di- and tri-glycerides, for example caprylic and capric tri-glycerides, and a mixture thereof.

In yet another particular embodiment, the formulation according to the invention comprises an animal oil. This animal oil may be selected, for example, from the group consisting of mink oil, sperm whale oil, whale oil, seal oil, emu oil, neatsfoot oil, fish oils, in particular anchovy oil, sardine oil, caplin oil, herring oil, salmon oil, sprat oil, cod oil, blue whiting oil, pilchard oil, tuna oil, shark oil, and a mixture thereof.

In a preferred embodiment, the formulation according to the invention comprises a vegetable oil. Examples of vegetable oils that may be used include, without it being limited thereto, wheatgerm oil, corn oil, sunflower oil, shear oil, castor oil, sweet almond oil, macadamia oil, apricot oil, soybean oil, cotton oil, alfalfa oil, poppy seed oil, pumpkin seed oil, sesame oil, marrow seed oil, avocado oil, hazelnut oil, grapeseed oil, blackcurrent seed oil, evening primrose oil, millet oil, barley oil, quinoa oil, olive oil, groundnut oil, rye oil, safflower oil, candlenut oil, passion flower oil, musk rose oil, coconut oil, argan oil, rapeseed oil, coconut kernel oil, linseed oil, walnut oil, cashew nut oil, margosa oil, pistachio oil, rice oil, camelina oil, sacha inchi oil, borage oil, hemp oil, pea oil, jojoba oil, neem oil, black cumin oil, perilla oil, and a mixture thereof.

In a most particularly preferred embodiment, the pharmaceutically acceptable oil included in the formulation according to the invention is a groundnut oil.

β-Lactamase Inhibitor

The pharmaceutical formulation according to the invention may also comprise one or more β-lactamase inhibitors. These inhibitors may block the activity of β-lactamases in various ways, for example by acting as a suicide substrate by irreversibly binding to these enzymes, as is the case especially for clavulanic acid and sulbactam.

The β-lactamase inhibitor may be any pharmaceutically acceptable β-lactamase inhibitor. This inhibitor is preferably selected from the group consisting of clavulanic acid, sulbactam, tazobactam, aztreonam, avibactam, pharmaceutically acceptable salts thereof, and mixtures thereof.

In a preferred embodiment, the formulation according to the invention comprises clavulanic acid. Clavulanic acid (CAS No.: 58001-44-8) is commonly used in combination with β-lactamine antibiotics, especially amoxicillin.

In the formulation according to the invention, clavulanic acid may be in any pharmaceutically acceptable form, preferably in the form of a pharmaceutically acceptable salt, especially in the form of a potassium salt of clavulanic acid.

Pharmaceutical Formulation

According to a first aspect, the present invention relates to a pharmaceutical formulation in powder form comprising, or consisting essentially of, cineole, amoxicillin, and a pharmaceutically acceptable oil.

As used herein, the term "powder" refers to a fractionated state of matter; it is a solid state in the form of small particles.

Preferably, the powder particles have a diameter of less than or equal to about 5 mm, more preferably less than or equal to about 2.5 mm and most particularly preferably less than or equal to about 1.25 mm.

The powder of the pharmaceutical formulation according to the invention is preferably a dry powder. As used herein, the term "dry powder" refers to a powder with a moisture content of less than or equal to 20%, preferably less than or equal to 15%, more preferably less than or equal to 10%.

The pharmaceutical formulation according to the invention preferably meets the requirements of the European Pharmacopea (8th edition), especially in terms of impurities and/or in terms of microbiological quality.

In particular, the content of bacteria present in the powder of the pharmaceutical formulation according to the invention is preferably less than 10000 CFU (colony-forming units) per gram of powder, preferably less than 1000 CFU per gram of powder, and most particularly preferably less than 100 CFU per gram of powder. Preferably, the powder of the pharmaceutical formulation according to the invention does not contain any *Escherichia coli*. As regards the other germs, the contents of fungi and yeasts is preferably less than 1000 CFU per gram of powder, preferably less than 100 CFU per gram of powder, and most particularly preferably less than 50 CFU per gram of powder.

The pharmaceutical formulation according to the invention comprises, or consists essentially of, cineole, amoxicillin, and a pharmaceutically acceptable oil, as defined above.

Preferably, amoxicillin and cineole are present in the formulation according to the invention at concentrations allowing the administration of doses that are sufficient to obtain a therapeutic effect and/or an antibacterial effect, preferably a synergistic effect, as illustrated in the examples below. To obtain such an effect, amoxicillin and cineole may be administered in therapeutically effective amounts or in sub-therapeutic amounts.

In a preferred embodiment, cineole and amoxicillin are both administered in therapeutically effective amounts.

According to another preferred embodiment, amoxicillin is administered in a therapeutically effective amount and cineole is administered in a sub-therapeutic amount.

In yet another preferred embodiment, amoxicillin is administered in a sub-therapeutic amount and cineole is administered in a therapeutically effective amount.

In yet another preferred embodiment, amoxicillin and cineole are both administered in sub-therapeutic amounts.

Preferably, the oil is present in the formulation according to the invention at a concentration sufficient to allow the adsorption of cineole onto the powder of the formulation.

According to one embodiment, the pharmaceutical formulation according to the invention comprises, or consists essentially of, between about 5 mg and about 100 mg, preferably between about 10 mg and about 50 mg, and more preferably between about 20 mg and about 40 mg of cineole by gram of powder; and/or between about 20 mg and about 500 mg, preferably between about 50 mg and 300 mg, and more preferably between about 150 mg and about 200 mg of amoxicillin per gram of powder; and/or between about 2 mg and about 50 mg, preferably between about 10 mg and about 25 mg, and more preferably between about 15 mg and about 20 mg of oil per gram of powder.

Preferably, the pharmaceutical formulation according to the invention comprises, or consists essentially of, between about 5 mg and about 100 mg of cineole, between about 20 mg and about 500 mg of amoxicillin, and between about 2 mg and about 50 mg of oil per gram of powder.

In a more preferred manner, the pharmaceutical formulation according to the invention comprises, or consists essentially of, between about 10 mg and about 50 mg of cineole, between about 50 mg and about 300 mg of amoxicillin, and between about 10 mg and about 25 mg of oil per gram of powder.

Most particularly preferably, the pharmaceutical formulation according to the invention comprises, or consists essentially of, between about 20 mg and about 40 mg, preferably about 33 mg, of cineole per gram of powder, between about 150 mg and about 200 mg, preferably about 167 mg, of amoxicillin per gram of powder, between about 15 mg and about 20 mg, preferably about 17 mg, of oil per gram of powder.

In a preferred embodiment, the pharmaceutical formulation according to the invention comprises, or consists essentially of, cineole, amoxicillin, a pharmaceutically acceptable oil and a β-lactamase inhibitor, as defined above.

Preferably, the β-lactamase inhibitor is selected from clavulanic acid, sulbactam, tazobactam and aztreonam. More preferably, the β-lactamase inhibitor is clavulanic acid.

Thus, the pharmaceutical formulation according to the invention may comprise, or consist essentially of, cineole, amoxicillin and a pharmaceutically acceptable oil in proportions as described above, and a β-lactamase inhibitor which is present in a concentration sufficient to allow its administration in a therapeutically effective amount or in a sub-therapeutic amount.

According to one embodiment, the pharmaceutical formulation according to the invention comprises, or consists essentially of, cineole, amoxicillin and a pharmaceutically acceptable oil in proportions as described above, and between about 1 mg and about 100 mg, preferably between about 5 mg and about 50 mg, more preferably between about 15 mg and about 25 mg, and most particularly preferably about 20.8 mg, of β-lactamase inhibitor, preferably clavulanic acid, per gram of powder.

In another particular embodiment, the pharmaceutical formulation according to the invention comprises, or consists essentially of, cineole, amoxicillin and a pharmaceutically acceptable oil, in which the proportion of cineole is between about 0.02 mg and about 0.5 mg, preferably between about 0.1 mg and about 0.3 mg, of cineole per gram of amoxicillin, and more preferably the proportion of cineole is equal to about 0.2 mg of cineole per gram of amoxicillin; and/or the proportion of oil is between about 0.01 mg and about 0.5 mg, preferably between about 0.05 mg and about 0.2 mg, of oil per gram of amoxicillin, and more preferably the proportion of oil is equal to about 0.1 mg of oil per gram of amoxicillin. Preferably, the pharmaceutical formulation according to the invention also comprises a β-lactamase inhibitor, preferably clavulanic acid, the proportion of β-lactamase inhibitor being between about 0.01 mg and about 0.5 mg, preferably between 0.1 mg and about 0.2 mg, of β-lactamase inhibitor per gram of amoxicillin, and more preferably the proportion of β-lactamase inhibitor is equal to about 0.125 mg of β-lactamase inhibitor per gram of amoxicillin.

In particular embodiments, the amoxicillin/cineole mass ratio is between 2 and 8, preferably between 3 and 7, more particularly preferably between 4 and 6. In a preferred embodiment, the amoxicillin/cineole mass ratio is about 5.

In particular embodiments, the mass ratio of amoxicillin/β-lactamase inhibitor, preferably clavulanic acid, is between 5 and 11, preferably between 6 and 10, more particularly preferably between 7 and 9. In a preferred embodiment, the mass ratio of amoxicillin/β-lactamase inhibitor, preferably clavulanic acid, is about 8.

In particular embodiments, the amoxicillin/oil mass ratio is between 5 and 15, preferably between 7 and 13, more particularly preferably between 8 and 12. In a preferred embodiment, the amoxicillin/cineole mass ratio is about 10.

In particular embodiments, the cineole/oil mass ratio is between 0.1 and 5, preferably between 0.5 and 4, more particularly preferably between 1 and 3. In a preferred embodiment, the cineole/oil mass ratio is about 2.

The pharmaceutical formulation according to the invention may also comprise at least one other active principle.

Thus, in a particular embodiment, the pharmaceutical formulation according to the invention comprises, or consists essentially of, cineole, amoxicillin, a pharmaceutically acceptable oil, optionally a β-lactamase inhibitor, preferably clavulanic acid, as defined above, and another active principle. Preferably, the additional active principle of the formulation according to the invention is another antibiotic, in particular a β-lactamine antibiotic, and/or another β-lactamase inhibitor, and/or an antifungal agent, and/or an antiparasitic agent, and/or an analgesic agent.

The pharmaceutical formulation according to the invention may comprise, or consist essentially of, cineole, amoxicillin, a pharmaceutically acceptable oil, and optionally a β-lactamase inhibitor, preferably clavulanic acid, in amounts as described above and another active principle which is present in a concentration that is sufficient to allow its administration in a therapeutically effective amount or in a sub-therapeutic amount.

Excipients

The pharmaceutical formulation according to the invention may further comprise at least one pharmaceutically acceptable excipient or support in addition to the pharmaceutically acceptable oil.

This pharmaceutically acceptable excipient or support of the formulation according to the invention is preferably selected from the group consisting of a sweetener, a flavoring, an anticaking agent, a lubricant, a disintegrant, and a mixture thereof.

Thus, in a particular embodiment, the pharmaceutical formulation according to the invention further comprises at least one disintegrant.

As used herein, the term "disintegrant" refers to an excipient which makes it possible to improve the disintegration, i.e. the separation of the molecules present in the pharmaceutical formulation in liquid medium, preferably an aqueous medium, and their homogeneous suspension.

Preferably, the disintegrant is selected from the group consisting of microcrystalline celluloses, crosslinked carboxymethyl starches, crosslinked polyvinylpyrrolidones and crosslinked carboxymethylcelluloses.

As used herein, the terms "crosslinked carboxymethylcellulose" and "croscarmellose" are equivalent and may be used interchangeably.

In another preferred embodiment, the pharmaceutical formulation according to the invention comprises between about 10 mg and about 1000 mg, preferably between about 100 mg and about 600 mg, more preferably between about 450 mg and about 550 mg, for example about 513.7 mg, of disintegrant per gram of powder.

In particular, the formulation may comprise a microcrystalline cellulose, preferably in the form of a powder consisting of particles with a diameter from about 20 to about 200 μm, more preferably a diameter from about 50 to about 100 μm. In particular, the microcrystalline cellulose is selected from microcrystalline celluloses of Avicel®, Emcocel® and Vitacel® type, or mixtures thereof; preferably, the microcrystalline cellulose is selected from the microcrystalline celluloses Avicel PH 101, 102, 103, 104, 112, 113, 301 and 302, and most particularly preferably the microcrystalline cellulose is of Avicel PH 112 type.

Thus, in a particular embodiment, the pharmaceutical formulation according to the invention comprises between about 100 mg and about 800 mg, preferably between about 300 mg and about 500 mg, more preferably between about 400 mg and about 420 mg, for example about 413.7 mg, of microcrystalline cellulose per gram of powder.

Alternatively, the formulation may comprise a croscarmellose. In particular, the croscarmellose may be in the form of a powder formed from particles with a mean diameter of less than 36 μm. Preferably, the croscarmellose is a croscarmellose sodium.

In another particular embodiment, the pharmaceutical formulation according to the invention comprises between about 10 mg and about 250 mg, preferably between about 50 mg and about 150 mg, more preferably between about 80 mg and 120 mg, for example about 100 mg, of croscarmellose per gram of powder.

According to a particularly preferred embodiment, the pharmaceutical formulation according to the invention comprises microcrystalline cellulose and croscarmellose as defined above. Thus, the pharmaceutical formulation according to the invention may comprise between about 100 mg and about 800 mg, preferably between about 300 mg and about 500 mg, more preferably between about 400 mg and about 420 mg, for example about 413.7 mg, of microcrystalline cellulose per gram of powder; and/or between about 10 mg and about 250 mg, preferably between about 50 mg and about 150 mg, more preferably between about 80 mg and 120 mg, for example about 100 mg, of croscarmellose per gram of powder.

The pharmaceutical formulation according to the invention may also comprise at least one excipient of anticaking agent type.

As used herein, the term "anticaking agent" refers to an excipient which limits the agglutination of the particles in a powder product and thus ensures its fluidity.

Preferably, the anticaking agent is selected from the group consisting of talc, silica and derivatives thereof, sodium carbonate, ammonium carbonate, ammonium bicarbonate, magnesium carbonate, sodium ferrocyanide, potassium ferrocyanide, calcium ferrocyanide, or mixtures thereof.

More preferably, the anticaking agent is selected from the group consisting of silica and derivatives thereof, in particular silica, colloidal silica, silicon dioxide, calcium silicate, magnesium silicate, sodium aluminosilicate, potassium aluminosilicate, calcium aluminosilicate, zinc silicate, aluminum silicate, or mixtures thereof.

Most particularly preferably, the anticaking agent is silica, preferably amorphous synthetic silica, in particular Syloid® A1-1 FP.

In a preferred embodiment, the pharmaceutical formulation according to the invention comprises between about 20 mg and about 500 mg, preferably between about 50 mg and about 300 mg, more preferably between about 150 mg and about 200 mg, for example about 180 mg of anticaking agent, preferably silica, per gram of powder.

The pharmaceutical formulation according to the invention may also comprise at least one excipient of lubricant type.

As used herein, the term "lubricant" refers to an excipient intended to facilitate the steps for manufacturing the powder, in particular by virtue of its glidant, non-stick and anti-friction effects.

Preferably, the lubricant is selected from the group consisting of magnesium stearate, aluminum stearate, calcium stearate, sodium stearate, zinc stearate, sodium stearylfumarate, propylene glycol, glyceryl monostearate or mixtures thereof. More preferably, the lubricant is magnesium stearate.

According to a preferred embodiment, the pharmaceutical formulation according to the invention comprises between about 1 mg and about 40 mg, preferably between about 2 mg and about 15 mg, more preferably between about 4 mg and about 10 mg, for example about 6 mg of lubricant, preferably magnesium stearate, per gram of powder.

The pharmaceutical formulation according to the invention may also comprise at least one excipient of sweetener type.

As used herein, the term "sweetener" refers to an excipient that is intended to change the taste of a pharmaceutical formulation by giving it a sweet taste.

Preferably, the sweetener is selected from the group consisting of acesulfame potassium (E950), alitame (E956), aspartame (E951), cyclamate (E952), neotame, saccharin (E954), the aspartame-acesulfame salt (E962), sucralose, thaumatine, polyols, brazzein, curculin, glycyrrhizin, a hydrogenated starch hydrolyzate, mabinlin, miraculin, monellin, pentadin, stevia, tagatose, trehalose, isomaltulose, erythritol, and mixtures thereof. Particularly preferably, the sweetener is aspartame.

According to a preferred embodiment, the pharmaceutical formulation according to the invention comprises between about 1 mg and about 60 mg, preferably between about 3 mg and about 20 mg, more preferably the pharmaceutical formulation of the invention comprises between about 8 mg and about 15 mg, for example about 12 mg of sweetener, preferably aspartame, per gram of powder.

The pharmaceutical formulation according to the invention may also comprise at least one excipient of flavoring type.

As used herein, the term "flavoring" refers to an excipient which is intended to change the taste of a pharmaceutical formulation by giving it a flavor.

Preferably, the flavoring is selected from the group consisting of strawberry, raspberry, cherry, banana, lemon, orange, peach, apple, caramel flavor, or mixtures thereof. More preferably, the flavoring is a mixture of lemon, strawberry and peach flavors.

According to a preferred embodiment, the pharmaceutical formulation according to the invention comprises between about 1 mg and about 100 mg, preferably between about 10 mg and about 50 mg, more preferably between about 20 mg and about 40 mg, for example about 30 mg, of flavoring per gram of powder.

In order to prevent the risks of microbiological contamination, the pharmaceutical formulation according to the invention may also comprise a preserving agent.

The preserving agents that may be used in the formulation according to the invention comprise, without being limited thereto, benzoic acid and the sodium or potassium salts thereof such as sodium benzoate; parabens such as methyl paraben, propyl paraben or butyl paraben; sorbic acid and the sodium or potassium salts thereof such as potassium sorbate; quaternary ammoniums such as benzalkonium chloride; mercury derivatives such as phenylmercury salts (acetate, borate or nitrate) or thiomersal; and a combination thereof.

The pharmaceutical formulation according to the invention may also comprise an excipient of pH buffer type, such as various acids and salts thereof, for instance citric acid, sodium citrate and succinic acid.

The formulation may also comprise a colorant, especially so as to increase its acceptability to children. Preferably, the colorant is used to reinforce the credibility of the flavor (for example a pink colorant for a strawberry flavor).

In a particularly preferred embodiment, the pharmaceutical formulation according to the invention does not comprise any detergent. The term "detergent" (or "surfactant"), as used herein refers to an amphiphilic molecule which has surfactant properties. Detergents that are commonly used in pharmaceutical formulations are, for example, ionic detergents such as sodium dodecyl sulfate (SDS), deoxycholate and cholate, nonionic detergents such as Triton X-100, n-dodecyl β-D-maltopyranoside (DDM), digitonin, Tween 20 and Tween 80, and amphoteric detergents such as 3-[(3-cholamidopropyl)dimethylammonio]-1-propanesulfonate (CHAPS) or 3-[dimethylammonio]-1-propanesulfonate.

In another preferred embodiment, the pharmaceutical formulation according to the invention is in the form of a powder comprising, or consisting essentially of, or consisting of, cineole, amoxicillin, a pharmaceutically acceptable oil, and at least a sweetener, a flavoring, an anticaking agent, a lubricant and/or a disintegrant as defined above and, optionally, a β-lactamase inhibitor, preferably clavulanic acid, as defined above.

Preferably, the pharmaceutical formulation according to the invention is in the form of a powder comprising, or consisting essentially of, or consisting of, cineole, amoxicillin, and oil in the proportions described above, and between about 1 mg and about 60 mg of sweetener, preferably aspartame, and/or between about 1 mg and about 60 mg of flavoring, and/or between about 20 mg and about 500 mg of anticaking agent, preferably silica, and/or between about 1 mg and about 40 mg of lubricant, preferably magnesium stearate, and/or between about 10 mg and about 1000 mg of disintegrant, preferably a mixture of microcrystalline cellulose and croscarmellose, per gram of powder and, optionally, a β-lactamase inhibitor, preferably clavulanic acid, in the proportions described above.

More preferably, the pharmaceutical formulation according to the invention is in the form of a powder comprising, or consisting essentially of, or consisting of, cineole, amoxicillin, and oil in the proportions described above, and between about 3 mg and about 20 mg of sweetener, preferably aspartame, and/or between about 10 mg and about 50 mg of flavoring, and/or between about 50 mg and about 300 mg of anticaking agent, preferably silica, and/or between about 2 mg and about 15 mg of lubricant, preferably magnesium stearate, and/or between about 100 mg and about 600 mg of disintegrant, preferably a mixture of microcrystalline cellulose and croscarmellose, per gram of powder, and, optionally, a β-lactamase inhibitor, preferably clavulanic acid, in the proportions described above.

Most particularly preferably, the pharmaceutical formulation according to the invention is in the form of a powder comprising, or consisting essentially of, or consisting of, cineole, amoxicillin, and oil in the proportions described above, and between about 8 mg and about 15 mg, for example about 12 mg, of sweetener, preferably aspartame, and/or between about 20 mg and about 40 mg, for example about 30 mg, of flavoring per gram of powder, and/or between about 150 mg and about 200 mg, for example about 180 mg, of anticaking agent, preferably silica, and/or between about 4 mg and about 8 mg, for example about 6 mg of lubricant, preferably magnesium stearate, and/or between about 450 mg and about 550 mg, for example about 513.7 mg, of disintegrant, for example about 100 mg of croscarmellose and about 413.7 mg of microcrystalline cellulose, and, optionally, a β-lactamase inhibitor, preferably clavulanic acid, in the proportions described above.

Packaging, Stability and Administration Route of the Formulation According to the Invention The inventors have demonstrated that the pharmaceutical formulation according to the invention is particularly stable. The stability of the product is characterized in that the amount of said product does not vary over a given time interval under the effect of various environmental factors, in particular the temperature and the humidity (ICH standard). The absence of variation may be observed for a final percentage of amoxicillin, cineole and optionally clavulanic acid which has not varied, preferably, by more than 5% relative to the initial values.

Thus, in a particular embodiment, the pharmaceutical formulation according to the invention is stable for at least 18 months, preferably for at least 24 months, more preferably for at least 36 months at a temperature of about 25° C. and under a relative humidity of at least about 60%.

In another particular embodiment, the pharmaceutical formulation according to the invention is stable for at least 6 months, preferably for at least 12 months, more preferably for at least 24 months at a temperature of about 30° C. and under a relative humidity of at least about 65%.

In yet another particular embodiment, the pharmaceutical formulation according to the invention is stable for at least 3 months, preferably for at least 6 months, more preferably for at least 12 months at a temperature of about 40° C. and at a relative humidity of at least about 75%.

Climatic chambers, which are well known to those skilled in the art, make it possible to subject the pharmaceutical formulation according to the invention to the temperature and relative humidity conditions mentioned above.

As used herein, the term "relative humidity" refers to the ratio of the partial pressure of water vapor contained in the air to the saturating vapor pressure (or vapor tension) at the same temperature.

The pharmaceutical formulation according to the invention is intended for oral administration.

Preferably, the pharmaceutical formulation is administered after suspension in an aqueous solvent followed by mixing; preferably, the aqueous solvent is water. Particularly preferably, the pharmaceutical formulation is dissolved extemporaneously. The pharmaceutical formulation according to the invention is stable after suspension in an aqueous medium, for at least 48 hours, preferably for at least 72 hours, more preferably for at least 96 hours at a temperature of less than or equal to about 20° C. and under a relative humidity of less than or equal to about 15%.

After suspending in an aqueous solvent, preferably water, the pharmaceutical formulation of the invention may form a solution with a slightly acidic pH. Preferably, the pH of the solution formed by the suspension of the pharmaceutical formulation of the invention in an aqueous solvent is between a pH of about 5 and a pH of about 7.

The pharmaceutical formulation according to the invention may be packaged in a single-dose or multi-dose container, preferably in a single-dose container.

In a preferred embodiment, the pharmaceutical formulation according to the invention is packaged in a single-dose container containing between about 1 g and about 150 g of powder, more preferably between about 1 g and about 50 g of powder, still preferably between about 1 g and about 10 g of powder, and more particularly preferably about 3 g of powder.

When the pharmaceutical formulation is packaged in a single-dose container, said single-dose containers may be secondarily packaged in a box. A box may contain, for example, between 3 and 31 single-dose containers, preferably between 5 and 21 single-dose containers, more preferably between 7 and 14 single-dose containers.

In another embodiment, the pharmaceutical solution according to the invention is packaged in a multi-dose container. Said container may contain, for example, between about 10 grams and about 500 grams of powder, preferably between about 20 grams and about 200 grams of powder, more preferably between about 30 grams of powder and about 100 grams of powder, and most particularly preferably about 50 grams of powder.

When the pharmaceutical formulation is packaged in a multi-dose container, said container may be secondarily packaged in a box, optionally accompanied by a doser, for example a spoon, for taking up a determined amount of powder, preferably from about 1 mg to about 30 mg of powder, more preferably from about 2 mg to about 20 mg of powder, and more preferably from about 3 to about 12 mg of powder. In particular, the doser may make it possible to take up about 3 g, about 6 g, about 9 g, about 12 g, about 15 g and/or about 18 g of powder.

Combination of Cineole and Amoxicillin

In a second aspect, the present invention also relates to a composition comprising, or consisting essentially of, cineole and amoxicillin for use in the treatment of a bacterial infection in an individual.

Preferably, in the combination according to the invention, amoxicillin and cineole are administered at doses making it possible to obtain a therapeutic effect and/or an antibacterial effect, preferably a synergistic effect, as illustrated in the examples below. To obtain such an effect, amoxicillin and/or cineole may be administered in therapeutically effective amounts or in sub-therapeutic amounts.

In a preferred embodiment, cineole and amoxicillin are both administered in therapeutically effective amounts.

In another preferred embodiment, amoxicillin is administered in a therapeutically effective amount and cineole is administered in a sub-therapeutic amount.

In yet another preferred embodiment, amoxicillin is administered in a sub-therapeutic amount and cineole is administered in a therapeutically effective amount.

In yet another preferred embodiment, amoxicillin and cineole are both administered in sub-therapeutic amounts.

According to one embodiment, cineole may be administered to the individual in a dose of between about 0.1 mg/kg/day and about 50 mg/kg/day, preferably between about 0.5 mg/kg/day and about 20 mg/kg/day, and most particularly preferably between about 1 mg/kg/day and about 10 mg/kg/day of weight of the individual; and/or amoxicillin may be administered to the individual in a dose of between about 5 mg/kg/day and about 200 mg/kg/day, preferably between about 10 mg/kg/day and about 100 mg/kg/day, and most particularly preferably between about 15 mg/kg/day and about 50 mg/kg of weight of the individual per day.

Preferably, the cineole of the combination according to the invention is administered to the individual at a dose of between about 0.1 mg/kg/day and about 50 mg/kg/day and the amoxicillin of the combination according to the invention is administered to the individual at a dose of between about 5 mg/kg/day and about 200 mg/kg of weight of the individual per day.

More preferably, the cineole of the combination according to the invention is administered to the individual at a dose of between about 0.5 mg/kg/day and about 20 mg/kg/day and the amoxicillin of the combination according to the invention is administered to the individual at a dose of between about 10 mg/kg/day and about 100 mg/kg of weight of the individual per day.

Most particularly preferably, the cineole of the combination according to the invention is administered to the individual at a dose of between about 1 mg/kg/day and about 10 mg/kg/day and the amoxicillin of the combination according to the invention is administered to the individual at a dose of between about 15 mg/kg/day and about 50 mg/kg of weight of the individual per day.

In a preferred embodiment, the combination according to the invention comprises, or consists essentially of, cineole, amoxicillin and a β-lactamase inhibitor, preferably selected from clavulanic acid, sulbactam, tazobactam and aztreonam, and mixtures thereof, for use in the treatment of a bacterial infection in an individual. Preferably, the β-lactamase inhibitor is clavulanic acid.

Thus, the cineole and amoxicillin of the combination according to the invention may be administered to the individual in amounts as described above and the β-lactamase inhibitor may be administered to the individual in a therapeutically effective amount or in a sub-therapeutic amount.

According to a particular embodiment, the cineole and amoxicillin of the combination according to the invention are administered to the individual at doses as described above and the β-lactamase inhibitor, preferably clavulanic acid, is administered to the individual at a dose of between about 0.1 mg/kg/day and about 50 mg/kg/day, preferably between about 0.5 mg/kg/day and about 20 mg/kg/day, and most particularly preferably between about 1 mg/kg/day and about 10 mg/kg of weight of the individual per day.

In another particular embodiment, the combination according to the invention comprises, or consists essentially of, cineole and amoxicillin, the proportion of cineole being between about 0.02 mg and about 0.5 mg, preferably between about 0.1 mg and about 0.3 mg, of cineole per gram of amoxicillin, and more preferably the proportion of cineole is equal to about 0.2 mg of cineole per gram of amoxicillin. Preferably, the combination according to the invention also comprises a β-lactamase inhibitor, preferably clavulanic acid, the proportion of β-lactamase inhibitor being between about 0.01 mg and about 0.5 mg, preferably between 0.1 mg and about 0.2 mg, of β-lactamase inhibitor per gram of amoxicillin, and more preferably the proportion of β-lactamase inhibitor is equal to about 0.125 mg of β-lactamase inhibitor per gram of amoxicillin.

The combination according to the invention may further comprise at least one other active principle. Preferably, the additional active principle of the combination according to the invention is another antibiotic, in particular a β-lactamine antibiotic, and/or another β-lactamase inhibitor, and/or an antifungal agent, and/or an antiparasitic agent, and/or an analgesic agent.

Thus, cineole, amoxicillin and optionally a β-lactamase inhibitor, preferably clavulanic acid, of the combination according to the invention may be administered in amounts as described above and the other active principle(s) may be administered to the individual in therapeutically effective amounts or in sub-therapeutic amounts.

Packaging and Administration Route of the Combination According to the Invention The active principles of the combination according to the invention may be administered to the individual simultaneously, sequentially, separately or via a mixture of these modes of administration.

When active principles of the combination according to the invention are administered sequentially or separately, the time interval(s) are preferably chosen so as to allow the desired therapeutic effect to be obtained, preferably with a synergistic effect between cineole and amoxicillin.

Preferably, the active principles of the combination according to the invention are administered simultaneously. When the administration of the active principles of the combination according to the invention is simultaneous, it preferably takes place by administration of a single formulation comprising all of the active principles of the combination.

When the combination according to the invention comprises more than two active principles, certain active principles may be administered simultaneously, certain active principles may be administered sequentially, and/or certain active principles may be administered separately. For example, when the combination according to the invention comprises three active principles, two active principles may be administered simultaneously and the third administered sequentially or separately, preferably sequentially.

In a particular embodiment, the combination according to the invention comprises cineole and amoxicillin administered to the individual simultaneously, preferably from a pharmaceutical composition comprising cineole and amoxicillin, alternatively from two pharmaceutical compositions, one comprising cineole and the other comprising amoxicillin.

In another particular embodiment, the combination according to the invention comprises cineole and amoxicillin administered to the individual sequentially or separately, preferably sequentially, from two pharmaceutical compositions, one comprising cineole and the other comprising amoxicillin.

In yet another particular embodiment, the combination according to the invention comprises cineole, amoxicillin and a β-lactamase inhibitor, preferably clavulanic acid, administered to the individual simultaneously. The cineole, amoxicillin and the β-lactamase inhibitor may be administered to the individual simultaneously from:
(a) a pharmaceutical composition comprising cineole, amoxicillin and a β-lactamase inhibitor;
(b) a pharmaceutical composition comprising cineole and a pharmaceutical composition comprising amoxicillin and a β-lactamase inhibitor;
(c) a pharmaceutical composition comprising amoxicillin and a pharmaceutical composition comprising cineole and a β-lactamase inhibitor;
(d) a pharmaceutical composition comprising a β-lactamase inhibitor, and a pharmaceutical composition comprising cineole and amoxicillin; or
(e) a pharmaceutical composition comprising cineole, a pharmaceutical composition comprising amoxicillin, and a pharmaceutical composition comprising a β-lactamase inhibitor.

In yet another particular embodiment, the combination according to the invention comprises cineole, amoxicillin and a β-lactamase inhibitor, preferably clavulanic acid, administered to the individual sequentially or separately, preferably sequentially, from a pharmaceutical composition comprising cineole, a pharmaceutical composition comprising amoxicillin, and a pharmaceutical composition comprising a β-lactamase inhibitor.

In yet another particular embodiment, the combination according to the invention comprises cineole, amoxicillin and a β-lactamase inhibitor, preferably clavulanic acid, in which the amoxicillin and the β-lactamase inhibitor are administered to the individual simultaneously and the cineole is administered to the individual sequentially or separately, preferably sequentially, from:
(a) a pharmaceutical composition comprising cineole, a pharmaceutical composition comprising amoxicillin, and a pharmaceutical composition comprising a β-lactamase inhibitor; or
(b) a pharmaceutical composition comprising cineole and a pharmaceutical composition comprising amoxicillin and a β-lactamase inhibitor.

In yet another particular embodiment, the combination according to the invention comprises cineole, amoxicillin and a β-lactamase inhibitor, preferably clavulanic acid, in which the cineole and the β-lactamase inhibitor are administered to the individual simultaneously and the amoxicillin is administered to the individual sequentially or separately, preferably sequentially, from:
(a) a pharmaceutical composition comprising cineole, a pharmaceutical composition comprising amoxicillin, and a pharmaceutical composition comprising a β-lactamase inhibitor; or
(b) a pharmaceutical composition comprising amoxicillin and a pharmaceutical composition comprising cineole and a β-lactamase inhibitor.

In yet another particular embodiment, the combination according to the invention comprises cineole, amoxicillin and a β-lactamase inhibitor, preferably clavulanic acid, in which the amoxicillin and the cineole are administered to the individual simultaneously and the β-lactamase inhibitor is administered to the individual sequentially or separately, preferably sequentially, from:
(a) a pharmaceutical composition comprising cineole, a pharmaceutical composition comprising amoxicillin, and a pharmaceutical composition comprising a β-lactamase inhibitor; or
(b) a pharmaceutical composition comprising a β-lactamase inhibitor, and a pharmaceutical composition comprising cineole and amoxicillin.

In a preferred embodiment, amoxicillin and a β-lactamase inhibitor, preferably clavulanic acid, are administered to the individual simultaneously, preferably from a pharmaceutical composition comprising amoxicillin and a β-lactamase inhibitor.

In another preferred embodiment, cineole, amoxicillin and optionally a β-lactamase inhibitor, preferably clavulanic acid, are administered to the individual simultaneously, preferably from a pharmaceutical composition comprising cineole, amoxicillin and optionally a β-lactamase inhibitor, or from a pharmaceutical composition comprising cineole and a pharmaceutical composition comprising amoxicillin and optionally a β-lactamase inhibitor.

In yet another preferred embodiment, cineole is administered to the individual sequentially or separately, preferably sequentially relative to the amoxicillin and/or, optionally, relative to the β-lactamase inhibitor, preferably clavulanic acid.

The active principles of the combination according to the invention may be administered to the individual via identical or different routes. The administration routes generally depend on the pharmaceutical formulations used. The active principles of the combination according to the invention are preferably administered to the individual parenterally or enterally, preferably enterally, more preferably orally or rectally. Particularly preferably, the active principles of the combination according to the invention are administered to the individual orally.

In a particular embodiment, amoxicillin and, optionally, a β-lactamase inhibitor, preferably clavulanic acid, are administered to the individual orally and cineole is administered to the individual rectally.

In a preferred embodiment, amoxicillin, cineole and, optionally, a β-lactamase inhibitor, preferably clavulanic acid, are administered to the individual orally.

The active principles of the combination according to the invention, in particular amoxicillin, cineole, and optionally a β-lactamase inhibitor, preferably clavulanic acid, may be administered to the individual in the form of any pharmaceutical formulation, which is preferably compatible with parenteral or enteral administration, more preferably compatible with oral or rectal administration, and most particularly preferably compatible with oral administration.

The active principles of the combination according to the invention, in particular amoxicillin, cineole, and optionally a β-lactamase inhibitor, preferably clavulanic acid, may thus be formulated in the form of tablets, capsules, gel capsules, granulates, powder, suspensions, emulsions, solutions, polymers, nanoparticles, microspheres, suppositories, rectal capsules, enemas, gels, pastes, ointments, creams, plasters, potions, injectables, implants, sprays or aerosols.

In a preferred embodiment, the active principles of the combination according to the invention are formulated in powder form, preferably powders for drinkable aqueous suspensions.

In a particular embodiment, the active principles are formulated in the form of suppositories or rectal capsules.

In another particular embodiment, cineole is formulated in the form of oil, or in the form of a suppository or a rectal capsule, preferably in the form of encapsulated oil, and the other active principles are formulated in the form of powders, preferably powders for drinkable aqueous suspensions.

Treatment of an Infectious Pathology in an Individual

In another aspect, the present invention also relates to a pharmaceutical formulation according to the invention for use in the treatment of an infectious pathology in an individual. The invention also relates to a pharmaceutical formulation according to the invention for the preparation of a medicament intended for treating an infectious pathology. The invention also relates to a treatment method comprising the administration of a therapeutically effective amount of the formulation according to the invention to an individual in need thereof, in particular an individual suffering from an infectious pathology.

The present invention also relates to a combination according to the invention for use in the treatment of an infectious pathology, preferably a bacterial infection, in an individual. The invention also relates to a treatment method comprising the administration of a therapeutically effective amount of a combination according to the invention, preferably a combination of cineole, amoxicillin and clavulanic acid, to an individual in need thereof, in particular an individual suffering from an infectious pathology, preferably a bacterial infection.

Preferably, the infectious pathology is of bacterial origin, and more preferably the infectious pathology is caused by one or more bacteria that are resistant to antibiotics, in particular to antibiotics of the β-lactamine family. Preferably, the term "antibiotic-resistant bacterium" refers to a bacterium which, depending on the case, is insensitive or sparingly sensitive to antibiotics. Similarly, a bacterium that is resistant to antibiotics of the β-lactamine family is insensitive or sparingly sensitive to antibiotics of this family. A bacterial infection with a bacterium that is resistant to antibiotics of the β-lactamine family will therefore not be efficiently treated with antibiotics of this family.

In a preferred embodiment, the infectious pathology is caused by an amoxicillin-resistant bacterium. Preferably, the bacterium responsible for the infectious pathology is at least partially resistant to a combination of amoxicillin and clavulanic acid.

In another preferred embodiment, the bacterium responsible for the infectious pathology is a ß-lactamase-producing bacterium. ß-Lactamases are "active serine" inactivation enzymes (classes A, C and D) or metalloenzymes (class B) whose substrates are ß-lactamine antibiotics. Narrow-spectrum ß-lactamases are distinguished from broad-spectrum ß-lactamases (BSBL) that are capable of inhibiting a large number of different ß-lactamine antibiotics, in particular penicillins, including amoxicillin, cephalosporins of 1st, 2nd and 3rd generation (e.g. cefotaxim, ceftazidim) and 4th generation (e.g. cefepim) and monobactams (e.g. aztreonam).

In a particularly preferred embodiment, the bacterium responsible for the infectious pathology is a broad-spectrum ß-lactamase (BSBL) producing bacterium. In particular, a BSBL-producing bacterium that is insensitive to clavulanic acid. Alternatively, the bacterium produces BSBLs that are only partially inhibited with clavulanic acid. BSBL bacteria may be detected via tests that are well known to those skilled in the art, such as the double disk test, the combined disk method and the BSBL E-test.

The bacterial infection treated with the pharmaceutical formation or the combination of the invention may be selected from the group consisting of cystitis, in particular recurring acute cystitis, bacterial sinusitis, in particular acute maxillary sinusitis, otitis, in particular acute otitis media, bronchitis, in particular chronic and/or acute bronchitis, bronchopneumopathy, in particular chronic and/or acute bronchopneumopathy, pyelonephritis, upper genital tract infections, parodontitis, severe stomatological infections, in particular abscesses, phlegmons and cellulites, animal bites, bone and joint infections, in particular osteomyelitis, endocarditis, pericarditis, septicemia, and dermal infections. Preferably, said bacterial infection is a cystitis, more preferably a cystitis that is resistant to antibiotics of the β-lactamine family, more preferably an amoxicillin-resistant cystitis, and most particularly preferably a cystitis that is resistant to a combination of amoxicillin and clavulanic acid.

The terms "individual" and "patient" are equivalent and may be used interchangeably in the context of the present invention. As used herein, the term "individual" refers to an animal, preferably a mammal, and more preferably the term "individual" refers to a human.

Thus, in a particular embodiment, the individual to which the formulation or combination according to the invention is administered is a human. It may thus be a newborn, a child, an adolescent, an adult or an elderly person. As used herein, the term "newborn" refers to a human being less than 12 months old, preferably less than 6 months old, more preferably less than 3 months old. As used in the present invention, the term "child" refers to a human being from 1 to 12 years old, preferably a human being from 1 to 8 years old and more preferably a human being from 1 to 5 years old. As used herein, the term "adult" refers to a human being from 12 to 60 years old, preferably a human being from 15 to 60 years old, more preferably a human being from 18 to 60 years old. As used in the present invention, the term "elderly person" refers to a human being of 60 years old or more, preferably a human being of 65 years old or more, and more preferably a human being of 70 years old or more.

In a preferred embodiment, the individual to which the formulation according to the invention is administered is an adult human.

In the field of veterinary applications, the individual of the invention may be a non-human animal, preferably a pet or breeding animal, more preferably an animal selected from the group consisting of dogs, cats, cattle, sheep, rabbits, pigs, goats, equids, rodents, in particular hamsters and guinea pigs, non-human primates and poultry, preferably table hens, laying hens, cockerels and reproductive hens, guineafowl, turkeys, quails, ducks, geese and pigeons.

In a most particularly preferred embodiment, the present invention relates to a formulation or a combination according to the invention in the treatment of a cystitis that is resistant to antibiotics of the β-lactamine family in a human.

Dosage

The pharmaceutical formulation or combination according to the invention, used in the treatment of an infectious pathology, preferably a bacterial infection, in an individual, may be administered in a single dose (a single administration), or in several doses (several administrations) depending on the individual, his age, his state of health and the infection to be treated. When several doses (several administrations) of the pharmaceutical formulation or of the combination according to the invention are administered, they may be spread over one or more days. The pharmaceutical formulation or the combination according to the invention may thus be administered at a rate of a single dose (one administration) per day of administration of the treatment.

Preferably, the individual receives several doses (several administrations) of the pharmaceutical formulation or of the combination according to the invention per day of administration of the treatment. More preferably, the individual receives three does (three administrations) of the pharmaceutical formulation or of the combination according to the invention per day of administration of the treatment, preferably morning, afternoon and evening.

The number of doses (or administrations) received by the individual per day of administration may also vary over time. Thus, periods in which the individual receives a single dose (a single administration) per day of administration of the treatment may alternate with periods in which the individual receives several doses (several administrations) per day of administration of the treatment, preferably three doses (three administrations) spread over morning, afternoon and evening. In particular, the individual may receive one dose (one administration) in general a single dose referred to as a "loading dose" on the first day of the treatment, before receiving several doses (several administrations) referred to as "maintenance doses" per day of treatment on the following days, preferably three maintenance doses (three administrations) per day of treatment, preferably in the morning, afternoon and evening.

The loading dose, which is generally administered to the individual on the first day of the treatment, preferably in a single dosage intake, is a dose of the formulation according to the invention that is preferably greater than or equal to the maintenance doses; more preferably, the loading dose is greater than or equal to two maintenance doses when the individual receives at least two maintenance doses per day of treatment. Preferably, the loading dose is between about 5 g and about 20 g, more preferably between about 10 g and about 15 g, and most particularly preferably the loading dose is about 12 g. Preferably, the maintenance dose is between about 1 g and about 15 g, more preferably between about 3 g and about 6 g, and most particularly preferably the maintenance dose is about 3 g or about 6 g.

The pharmaceutical formulation or the combination according to the invention may be administered every day, every two days, or once a week, preferably every day. The periodicity of intake of the formulation or of the combination depends on various parameters and may be readily defined by a person skilled in the art depending on, for example, the intended overall duration of intake of the pharmaceutical formulation or of the combination, the age of the individual and/or the seriousness of the infection, preferably a bacterial infection, to be prevented or treated. The periodicity of intake (of administration) of the pharmaceutical formulation or of the combination may also change over time, in a given individual, especially as a function of the evolution of his infection, and/or of his overall state of health.

In particular, the pharmaceutical formulation or the combination according to the invention may be administered to the individual for a period ranging from 1 day to about 3 months, 2 months, 1 month, 3 weeks, 2 weeks, 1 week, 5 days, 3 days, 2 days, preferably for a period from about 2 to about 21 days, more preferably for a period from about 7 to about 14 days. In a particularly preferred embodiment, the pharmaceutical formulation or the combination according to the invention is administered to the individual for a period of about 7 days. Alternatively, the pharmaceutical formulation or the combination according to the invention may be administered throughout the duration of the infection. In the case of a urinary infection, the formulation or the combination according to the invention may be administered until sterile urine is obtained in the individual.

In a particular embodiment, the pharmaceutical formulation or the combination according to the invention may be administered for several months, optionally for several years, for example in the case of chronic bacterial infections.

The pharmaceutical formulation according to the invention may be administered to the individual at a rate from about 1 to about 150 grams, preferably from about 1 to about 50 grams, more preferably from about 2 to about 30 grams, most particularly preferably from about 3 to about 20 grams per day of treatment. For example, about 9 grams of the pharmaceutical formulation according to the invention may be administered to the individual per day of treatment. In another example, about 18 grams of the formulation according to the invention may be administered to the individual per day of treatment.

Pharmaceutical Composition of Cineole and Amoxicillin

The invention also relates, in another aspect, to a pharmaceutical composition comprising, or consisting essentially of, cineole, amoxicillin and a pharmaceutically acceptable excipient or support, and optionally a β-lactamase inhibitor.

In a preferred embodiment, the β-lactamase inhibitor is selected from clavulanic acid, sulbactam, tazobactam and aztreonam; preferably, the β-lactamase inhibitor is clavulanic acid.

In a particular embodiment, the composition according to the invention comprises, or consists essentially of, cineole, amoxicillin, optionally a β-lactamase inhibitor, preferably clavulanic acid, and another active principle. Preferably, the additional active principle of the composition according to the invention is another antibiotic, in particular a β-lactamine antibiotic, and/or another β-lactamase inhibitor, and/or an antifungal agent, and/or an antiparasitic agent and/or an analgesic agent.

Preferably, the composition according to the invention comprises, or consists essentially of, active principles, preferably amoxicillin and cineole, which are present at concentrations allowing the administration of doses that are sufficient to obtain a therapeutic effect and/or an antibacterial effect, preferably a synergistic effect, as illustrated in the examples below. To obtain such an effect, amoxicillin and cineole may be administered in therapeutically effective amounts or in sub-therapeutic amounts.

In a preferred embodiment, cineole and amoxicillin are both administered in therapeutically effective amounts.

In another preferred embodiment, amoxicillin is administered in a therapeutically effective amount and cineole is administered in a sub-therapeutic amount.

In yet another preferred embodiment, amoxicillin is administered in a sub-therapeutic amount and cineole is administered in a therapeutically effective amount.

In yet another preferred embodiment, amoxicillin and cineole are both administered in sub-therapeutic amounts.

When they are present in the composition according to the invention, the β-lactamase inhibitor and/or the additional active principle may be administered in therapeutically effective amounts or in sub-therapeutic amounts.

The composition according to the invention may comprise, or consist essentially of, between about 5 mg and about 100 mg, preferably between about 10 mg and about 50 mg, more preferably between about 20 mg and about 40 mg, most particularly preferably about 33 mg, of cineole per gram of composition; and/or between about 20 mg and about 500 mg, preferably between about 50 mg and about 300 mg, more preferably between about 150 mg and about 200 mg, most particularly preferably about 167 mg, of amoxicillin per gram of composition; and/or optionally between about 1 mg and about 100 mg, preferably between about 5 mg and about 50 mg, more preferably between about 15 mg and about 25 mg, and most particularly preferably about 21 mg, of β-lactamase inhibitor, preferably clavulanic acid, per gram of composition.

Preferably, the composition according to the invention comprises, or consists essentially of, between about 5 mg and about 100 mg of cineole, between about 20 mg and about 500 mg of amoxicillin, and optionally between about 1 mg and about 100 mg of β-lactamase inhibitor, preferably clavulanic acid, per gram of composition.

More preferably, the composition according to the invention comprises, or consists essentially of, between about 10 mg and about 50 mg of cineole, between about 50 mg and about 300 mg of amoxicillin, and optionally between about 50 mg and about 50 mg of β-lactamase inhibitor, preferably clavulanic acid, per gram of composition.

Most particularly preferably, the composition according to the invention comprises, or consists essentially of, between about 20 mg and about 40 mg, preferably about 33 mg, of cineole, and between about 150 mg and about 200 mg, preferably about 167 mg, of amoxicillin, and optionally between about 15 mg and about 25 mg, and most particularly preferably about 21 mg, of β-lactamase inhibitor, preferably clavulanic acid, per gram of composition.

The composition according to the invention may be in the form of tablets, capsules, gel capsules, granulates, powder, suspensions, emulsions, solutions, polymers, nanoparticles, microspheres, suppositories, rectal capsules, enemas, gels, pastes, ointments, creams, plasters, potions, injectables, implants, sprays or aerosols. Preferably, the pharmaceutical composition according to the invention is in the form of a powder, more particularly a powder for a drinkable suspension.

Preferably, the technical characteristics of the powder are as defined previously for the pharmaceutical formulation according to the invention.

The composition according to the invention further comprises at least one pharmaceutically acceptable excipient or support. A person skilled in the art can readily define the excipients required for a composition as a function of the chosen pharmaceutical form.

In practice, when the composition according to the invention is in powder form, the pharmaceutically acceptable excipient or support of the composition according to the invention is preferably selected from the group consisting of a sweetener, a flavoring, an anticaking agent, a lubricant, a disintegrant, an adsorbent, and a mixture thereof.

Preferably, when the composition according to the invention is in powder form, the composition according to the invention comprises at least one sweetener, preferably aspartame, a flavoring, an anticaking agent, preferably silica, a lubricant, preferably magnesium stearate, a disintegrant, preferably a mixture of croscarmellose and microcrystalline cellulose, and an adsorbent, preferably oil. Such a composition may also comprise a preserving agent, a colorant and/or a pH buffer.

Thus, in a preferred embodiment, the composition according to the invention is in the form of a powder comprising, or consisting essentially of, or consisting of, cineole, amoxicillin, and at least one sweetener, a flavoring, an anticaking agent, a lubricant, a disintegrant and/or an adsorbent as defined above and optionally a β-lactamase inhibitor, preferably clavulanic acid, as defined above.

Preferably, the composition according to the invention is a powder comprising, or consisting essentially of, or consisting of, cineole and amoxicillin in the proportions described above, and between about 1 mg and about 60 mg of sweetener, preferably aspartame, and/or between about 1 mg and about 60 mg of flavoring, and/or between about 20 mg and about 500 mg of anticaking agent, preferably silica, and/or between about 1 mg and about 40 mg of lubricant, preferably magnesium stearate, and/or between about 10 mg and about 1000 mg of disintegrant, preferably a mixture of microcrystalline cellulose and croscarmellose, and/or between about 2 mg and about 50 mg of adsorbent, preferably oil, per gram of powder, and optionally a β-lactamase inhibitor, preferably clavulanic acid, in the proportions described above.

The composition according to the invention may especially comprise at least one excipient of adsorbent type. As used herein, the term "adsorbent" refers to an excipient that is capable of fixing liquid molecules, for example cineole molecules, to a solid support, for example a powdery support, in a pharmaceutical composition. Preferably, the adsorbent is a pharmaceutically acceptable oil. The pharmaceutically acceptable oil is as described previously.

In another particularly preferred embodiment, the composition according to the invention does not comprise any detergent. The detergent is as described previously in the chapter on excipients.

The invention also relates to a pharmaceutical composition according to the invention for use in the treatment of an infectious pathology, preferably a bacterial infection, in an individual.

The invention also relates to a treatment method comprising the administration of a therapeutically effective amount of the pharmaceutical composition according to the invention to an individual in need thereof, in particular an individual suffering from an infectious pathology, preferably a bacterial infection.

The embodiments and definitions described for the use of a combination according to the invention or of a pharmaceutical formulation according to the invention in the treatment of an infectious pathology, preferably a bacterial infection, in an individual and also as regards the dosage of this combination or formulation, are also to be taken into consideration in this aspect.

Preferably, the infectious pathology is caused by one or more bacteria that are resistant to antibiotics, preferably to antibiotics of the β-lactamine family, more preferably to amoxicillin and most particularly preferably to a combination of amoxicillin and clavulanic acid.

In a most particularly preferred embodiment, the present invention relates to a pharmaceutical composition according to the invention for use in the treatment of a cystitis, in particular a cystitis that is resistant to antibiotics, preferably to antibiotics of the β-lactamine family, more preferably to amoxicillin and most particularly preferably to a combination of amoxicillin and clavulanic acid.

Kit

The invention also relates, in another aspect, to a kit for treating an infectious pathology, preferably a bacterial infection, in an individual, comprising:
(a) a pharmaceutical composition comprising, or consisting essentially of, cineole and a pharmaceutically acceptable composition comprising, or consisting essentially of, amoxicillin;
(b) a pharmaceutical composition comprising, or consisting essentially of, cineole and a pharmaceutical composition comprising, or consisting essentially of, amoxicillin and a β-lactamase inhibitor, preferably clavulanic acid;

(c) a pharmaceutical composition comprising, or consisting essentially of, amoxicillin and a pharmaceutical composition comprising, or consisting essentially of, cineole and a β-lactamase inhibitor, preferably clavulanic acid;

(d) a pharmaceutical composition comprising, or consisting essentially of, a β-lactamase inhibitor, preferably clavulanic acid, and a pharmaceutical composition comprising, or consisting essentially of, cineole and amoxicillin; or (e) a pharmaceutical composition comprising, or consisting essentially of, cineole, a pharmaceutical composition comprising, or consisting essentially of, amoxicillin, and a pharmaceutical composition comprising, or consisting essentially of, a β-lactamase inhibitor, preferably clavulanic acid; and (f) optionally, a guide containing instructions for the use of such a kit.

Preferably, each composition included in the kit is in a separate recipient, container and/or packaging.

In a particular embodiment, at least one pharmaceutical composition of the kit according to the invention also comprises at least one other active principle. Preferably, the additional active principle according to the invention is another antibiotic, in particular a β-lactamine antibiotic, and/or another β-lactamase inhibitor, and/or an antifungal agent, and/or an antiparasitic agent, and/or an analgesic agent.

Preferably, the active principles of the compositions of the kit according to the invention, in particular amoxicillin and cineole, are present at concentrations allowing the administration of doses that are sufficient to obtain a therapeutic effect and/or an antibacterial effect, preferably a synergistic effect when said active principles are present in the same composition or when, present in different compositions, they are used simultaneously, sequentially or separately. To obtain such an effect, cineole and amoxicillin may be administered in therapeutically effective amounts or in sub-therapeutic amounts.

In a preferred embodiment, cineole and amoxicillin are both administered in therapeutically effective amounts.

In another preferred embodiment, amoxicillin is administered in a therapeutically effective amount and cineole is administered in a sub-therapeutic amount.

In yet another preferred embodiment, amoxicillin is administered in a sub-therapeutic amount and cineole is administered in a therapeutically effective amount.

In yet another preferred embodiment, amoxicillin and cineole are both administered in sub-therapeutic amounts.

When they are present in the compositions of the kit according to the invention, the β-lactamase inhibitor and/or the additional active principle may be administered in therapeutically effective amounts or in sub-therapeutic amounts.

The pharmaceutical composition of the kit according to the invention comprising cineole may comprise between about 5 mg and about 100 mg, preferably between about 10 mg and about 50 mg, more preferably between about 20 mg and about 40 mg, and most particularly preferably about 33 mg, of cineole per gram of composition.

The pharmaceutical composition of the kit according to the invention comprising amoxicillin may comprise between about 20 mg and about 500 mg, preferably between about 50 mg and about 300 mg, more preferably between about 150 mg and about 200 mg, and most particularly preferably about 167 mg, of amoxicillin per gram of composition.

When a pharmaceutical composition of the kit according to the invention comprises a β-lactamase inhibitor, preferably clavulanic acid, said composition may comprise between about 1 mg and about 100 mg, preferably between about 5 mg and about 50 mg, even more preferably about 15 mg to about 25 mg, and most particularly preferably about 21 mg, of β-lactamase inhibitor per gram of composition.

The compositions of the kit according to the invention are in the form of tablets, capsules, gel capsules, granulates, powder, suspensions, emulsions, solutions, polymers, nanoparticles, microspheres, suppositories, rectal capsules, enemas, gels, pastes, ointments, creams, pastes, potions, injectables, implants, sprays or aerosols.

Preferably, the pharmaceutical compositions according to the invention are in the form of powders, suppositories or rectal capsules, preferably in the form of powders, more preferably in the form of dry powders, more particularly dry powders for drinkable suspensions.

When cineole is the only active principle of a composition, it may be in oil form, in particular encapsulated oil.

The pharmaceutical composition(s) of the kit according to the invention preferably comprise at least one pharmaceutically acceptable excipient or support. A person skilled in the art can readily define the excipients required for a composition as a function of the chosen pharmaceutical form. The pharmaceutically acceptable excipients or support are as defined above for the pharmaceutical composition.

The invention relates, in yet another aspect, to a kit according to the invention for use in the treatment of an infectious pathology, preferably a bacterial infection, in an individual.

The embodiments and definitions described for the use of a formulation or a combination according to the invention in the treatment of an infectious pathology in an individual, and also regarding the administration and posology of this formulation or combination, are also to be taken into consideration in this aspect.

Preferably, the infectious pathology is caused by one or more bacteria that are resistant to antibiotics, preferably to antibiotics of the β-lactamine family, more preferably to amoxicillin and most particularly preferably to one or more bacteria that are at least partially resistant to a combination of amoxicillin and clavulanic acid.

In a most particularly preferred embodiment, the present invention relates to a pharmaceutical composition according to the invention for use in the treatment of a cystitis, in particular a cystitis that is resistant to antibiotics, preferably to antibiotics of the β-lactamine family, more preferably to amoxicillin and most particularly preferably to a combination of amoxicillin and clavulanic acid.

Process for Manufacturing the Pharmaceutical Formulation

The present invention also relates, in a third aspect, to a process for manufacturing the pharmaceutical composition or formulation according to the invention, comprising:
the production of a wetting solution by mixing cineole and a pharmaceutically acceptable oil;
wetting of a powder comprising amoxicillin with the wetting solution so as to obtain a powdery preparation comprising amoxicillin, cineole and oil.

The present invention also relates to the pharmaceutical composition or formulation obtained via the process according to the invention.

As used herein, the term "wetting solution" refers to a solution for wetting or humidifying a dry powder. The wetting operation may in particular be performed by spraying the wetting solution onto the powder to be wetted.

The step for obtaining a wetting solution of the process according to the invention may be performed by mixing cineole and a pharmaceutically acceptable oil as described previously in oil to cineole mass proportions of between about 0.1 and about 1, preferably between about 0.2 and about 0.8, more preferably between about 0.4 and about 0.6. Most particularly preferably, the oil to cineole mass proportion is about 0.5. For example, about 50 mg of oil is mixed with about 100 mg of cineole, or alternatively about 16.7 mg of oil is mixed with about 33.3 mg of cineole.

Preferably, the mixture of cineole and oil for obtaining a wetting solution is prepared in a closed chamber, preferably at a temperature not exceeding about 20° C. to avoid evaporation of the cineole, but sufficient to keep the mixture in liquid form.

In a particular embodiment, the powder comprising amoxicillin and intended to be wetted with the wetting solution also comprises a β-lactamase inhibitor, preferably selected from the group consisting of clavulanic acid, sulbactam, tazobactam, aztreonam and pharmaceutically acceptable salts thereof; more preferably, the β-lactamase inhibitor is clavulanic acid.

Preferably, the powder comprising amoxicillin and intended to be wetted with the wetting solution also comprises at least one pharmaceutically acceptable excipient or support, preferably selected from the group consisting of a sweetener, a flavoring, an anticaking agent, a lubricant, a disintegrant, and a mixture thereof. More preferably, the powder comprising amoxicillin comprises at least one sweetener, a flavoring, an anticaking agent, a lubricant and a disintegrant as defined above.

In another particular embodiment, the powder comprising amoxicillin and intended to be wetted with the wetting solution also comprises clavulanic acid, silica, colloidal silica, aspartame, croscarmellose, microcrystalline cellulose, magnesium stearate and a flavoring as defined above.

Preferably, the process according to the invention also comprises a step of compacting the powder comprising amoxicillin before it is wetted with the wetting solution. The granules obtained by compacting are preferably calibrated and then fractionated before wetting with the wetting solution.

In another embodiment, the process for manufacturing the pharmaceutical composition or formulation according to the invention comprises:
  the production of a wetting solution by mixing cineole and a pharmaceutically acceptable oil;
  the wetting of a powder comprising amoxicillin with a wetting solution so as to obtain a powdery preparation comprising amoxicillin, cineole and oil;
  mixing of the preparation obtained in the preceding step with a powder comprising a β-lactamase inhibitor, preferably selected from the group consisting of clavulanic acid, sulbactam, tazobactam, aztreonam and pharmaceutically acceptable salts thereof; more preferably, the β-lactamaseinhibitor is clavulanic acid;
  screening of the powder thus obtained.

In this process, the powder comprising amoxicillin and/or the powder comprising the β-lactamase inhibitor, preferably clavulanic acid, may also comprise a disintegrant as described above, preferably two disintegrants, in particular microcrystalline cellulose and croscarmellose. In a preferred embodiment, the powder comprising amoxicillin and the powder comprising a β-lactamase inhibitor, preferably clavulanic acid, comprise two disintegrants, microcrystalline cellulose and croscarmellose.

The powder comprising amoxicillin and/or the powder comprising a β-lactamase inhibitor, preferably clavulanic acid, may further comprise an anticaking agent as described above. In a preferred embodiment, the powder comprising amoxicillin and the powder comprising a β-lactamase inhibitor, preferably clavulanic acid, both comprise an anticaking agent, preferably silica.

In a most particularly preferred embodiment, the powder comprising amoxicillin and the powder comprising a β-lactamase inhibitor, preferably clavulanic acid, both comprise microcrystalline cellulose, croscarmellose and silica.

Thus, the process according to the invention may comprise a step of screening and then of mixing the disintegrant(s) and the anticaking agent. Alternatively, the disintegrant(s) and the anticaking agent may be mixed before the mixture is screened. In particular, the microcrystalline cellulose, croscarmellose and silica may be mixed in proportions from about 1000 mg to about 1500 mg, preferably about 1241 mg, of microcrystalline cellulose per about 200 mg to about 400 mg, preferably about 300 mg, of croscarmellose and from about 400 mg to about 600 mg, preferably about 540 mg, of silica.

The process according to the invention may also comprise a step of mixing these excipients with the powder comprising amoxicillin and/or with the powder comprising clavulanic acid; preferably, a portion of these excipients is mixed with the powder comprising amoxicillin and the other portion of these excipients with the powder comprising clavulanic acid.

In another preferred embodiment, the powder comprising a β-lactamase inhibitor, preferably clavulanic acid, also comprises colloidal silica, preferably in a mass proportion relative to the clavulanic acid of between about 0.7 and about 1.3, preferably about 0.9 and about 1.1, more preferably about 1. Preferably, the mixture of clavulanic acid and colloidal silica is prepared before adding any other excipient or mixing with the powder comprising amoxicillin.

Preferably, the process according to the invention also comprises a step of compacting the powder comprising amoxicillin before it is wetted with the wetting solution. The granules obtained by compacting are preferably calibrated and then fractionated before wetting with the wetting solution.

Similarly, the process according to the invention preferably comprises a step of compacting the powder comprising a β-lactamase inhibitor, preferably clavulanic acid, before it is mixed with the mixture of the amoxicillin powder wetted with the wetting solution. The granules obtained by compacting are preferably calibrated and then fractionated before wetting with the wetting solution.

During the step of wetting the powder comprising amoxicillin with the wetting solution, the wetting solution may be used in a proportion from about 100 to about 200 mg, preferably about 150 mg, of wetting solution for a powder comprising from about 400 to about 600 mg, preferably about 500 mg, of amoxicillin.

During the step of mixing the preparation of amoxicillin, cineole and oil with the powder comprising a β-lactamase inhibitor, preferably clavulanic acid, the preparation of amoxicillin, cineole and oil is mixed with a powder comprising from about 550 mg to about 750 mg, preferably about 650 mg, of β-lactamase inhibitor.

Optionally, the process of the invention may comprise, after the step of mixing the preparation of amoxicillin, cineole and oil with the powder comprising clavulanic acid, an additional step of adding a sweetener, a flavoring and/or a lubricant as described above. Preferably, a sweetener, a flavoring and a lubricant are added. Preferably, the sweetener is aspartame and the lubricant is magnesium stearate.

During this step, these additional excipients may be added in proportions from about 30 mg to about 50 mg, preferably about 36 mg, of sweetener, preferably aspartame, from about 15 mg to about 25 mg, preferably about 18 mg, of lubricant, preferably magnesium stearate, and/or from about 70 mg to about 110 mg, preferably 90 mg, of flavoring per 3 grams of pharmaceutical formulation.

After the step of adding a sweetener, a flavoring and/or a lubricant, the preparation obtained is mixed until a homogeneous powder is obtained.

In a preferred embodiment, the final screening step is performed with a screening mesh having apertures with a diameter of not more than 5 mm, preferably not more than 2.5 mm, more preferably not more than 1.25 mm.

Optionally, the process of the invention may comprise an additional step of packaging the screened powder obtained via the process of the invention in a single-dose or multi-dose container, preferably in a single-dose container.

In a preferred embodiment, the screened powder obtained via the process of the invention is packaged in a single-dose container containing between about 1 g and about 150 g of powder, more preferably between about 1 g and about 50 g of powder, preferably still between about 1 g and about 10 g of powder, and more particularly preferably about 3 g of powder.

In another embodiment, the screened powder obtained via the process of the invention is packaged in a multi-dose container comprising, for example, between about 10 grams and about 500 grams of powder, preferably between about 20 grams and about 200 grams of powder, more preferably between about 30 grams and about 100 grams of powder, and most particularly preferably about 50 grams of powder.

Optionally, the process of the invention may comprise an additional step of secondary packaging of the primary packaging for the screened powder obtained via the process of the invention.

In a preferred embodiment, said single-dose containers containing the screened powder are secondarily packaged in a box. In particular, a box may contain, for example, between 3 and 31 single-dose containers, preferably between 5 and 21 single-dose containers and more preferably between 7 and 14 single-dose containers.

In another embodiment, said multi-dose container containing the screened powder is secondarily packaged in a box, optionally accompanied with a doser, for example a spoon, for taking up a determined amount of powder, preferably from about 1 mg to about 30 mg of powder, more preferably from about 2 mg to about 20 mg of powder and most particularly preferably from about 3 to about 12 mg of powder. In particular, the doser may make it possible to take up about 3 g, about 6 g, about 9 g, about 12 g, about 15 g and/or about 18 g of powder.

Molecular Complex

Amoxicillin is a β-lactamase-sensitive antibiotic. β-Lactamases, which are produced by amoxicillin-resistant bacteria, recognize and inactivate the β-lactam core of amoxicillin. When it is placed in solution, preferably in an aqueous solvent, amoxicillin can transiently form complexes of two amoxicillin molecules. The formation of these complexes is too transient to have any protective effect against β-lactamases. However, when the pharmaceutical formulation of the invention is placed in solution, stable amoxicillin complexes comprising at least three amoxicillin molecules form and protect the antibiotic against the action of β-lactamases. The formation of these complexes may also be obtained by placing amoxicillin in solution in the presence of cineole.

Thus, in a final aspect, the invention also relates to a molecular complex comprising more than two amoxicillin molecules organized linearly or in a ring and interacting with each other via non-covalent bonds.

Preferably, the molecular complex of the invention is formed solely of amoxicillin molecules.

The molecular complex of the invention is formed from at least three amoxicillin molecules, preferably from three to six amoxicillin molecules, more preferably from three or four amoxicillin molecules and most particularly preferably from four amoxicillin molecules.

The amoxicillin molecules of the molecular complex of the invention may be organized linearly or in a ring. Preferably, they are organized in a ring so that each amoxicillin molecule interacts with two other amoxicillin molecules.

In a particular embodiment, the amoxicillin molecules can pass freely from an organization as a linear complex to an organization as a ring complex by breaking or forming non-covalent bonds.

The molecular complex of the invention may be obtained by placing amoxicillin in solution in the presence of cineole in an aqueous solvent. Preferably, the molecular complex of the invention is obtained by placing amoxicillin in solution in the presence of cineole in an aqueous solvent in the absence of detergent.

In a particular embodiment, the molecular complex of the invention is obtained by placing the pharmaceutical formulation of the invention in solution in an aqueous solvent.

Preferably, the amoxicillin molecules of the molecular complex of the invention are not recognized by β-lactamases. Thus, the molecular complex of the invention may be used in the treatment of bacteria considered as amoxicillin-resistant.

In a particular embodiment, the molecular complex of the invention may be obtained in aqueous medium when the mass ratio of amoxicillin to cineole is between about 0.01 and about 1000, preferably between about 0.1 and about 100, more preferably between about 1 and about 10, and most particularly preferably when the mass ratio of amoxicillin to cineole is about 5.

The present invention also relates to the use of the molecular complex according to the invention as a medicament. The invention also relates to the molecular complex according to the invention for use in the treatment of an infections pathology in an individual. The invention also relates to the molecular complex according to the invention for the preparation of a medicament intended for treating an infectious pathology. The invention also relates to a treatment method comprising the administration of a therapeutically effective amount of the molecular complex according to the invention to an individual in need thereof, in particular an individual suffering from an infectious pathology.

The embodiments described for the formulation or the combination according to the invention are also to be taken into account in this aspect.

All the references cited in the present patent application, including the journal articles or summaries, the published patent applications, the granted patents or any other reference, are entirely incorporated herein by reference, which includes all the results, tables, figures and texts presented in said references.

Although having different meanings, the terms "comprising", "having", "containing" and "consisting of" may be replaced with each other throughout the description of the invention.

Other characteristics and advantages of the invention will emerge more clearly on reading the examples which follow, which are given as nonlimiting illustrations.

EXAMPLES

Example 1—In Vitro Study of the Antibacterial Activity of the Combination of Amoxicillin and Cineole Materials and Methods
Biological Materials, Culture Medium and Antimicrobial Agents The six strains tested in this study are purified clinical isolates identified in the bacteriology laboratory of the Hassan II university teaching hospital center (CHU, Fes, Morocco). Three of the six bacterial strains tested are strains of BSBL *Escherichia coli* (P956, P933 and P7847) and the other three bacterial strains tested are strains of BSBL *Klebsiella pneumoniae* (H1878, H2001 and H1893).

For each test performed, precultures of the bacterial strains (frozen beforehand at −20° C.) for 24 h at 37° C. were prepared. From these precultures, bacterial inocula containing $2\times10^7$ CFU (colony-forming units)/ml were prepared, adjusting the optical density to 540 nm.

Liquid and agar Mueller-Hinton (MH) culture media were supplied by BIOKAR (France). The first was used for the growth of the strains and the second, supplemented with 20% (v/v) of glycerol, was used for storing the strains. The preparation of the two media was performed according to the supplier's instructions.

Amoxicillin (AMX) and cineole were supplied by Sigma Aldrich (France). A stock solution of AMX (400 µg/ml) was prepared after dissolving 40 mg of antibiotic in 100 ml of sterile distilled water. From this stock solution, serial dilutions were performed. The cineole concentrations used were prepared by emulsifying pure cineole in 0.2% (v/v) of agar-agar according to the method described by Remmal A et al. (J. Essent. Oil. Res [Book], 1993, 5: pages 1179-1184).

Evaluation of the Percentages of Inhibition of the Combination of AMX with Cineole The partial inhibitory concentrations (PIC) are the concentrations of antibacterial agents which inhibit the growth of a given percentage (90%, 75%, 50%, 40% . . . ) of the bacterial population studied. The PICs of AMX and cineole with respect to the six bacterial strains used were determined via a microplate microdilution technique based on the monitoring of the bacterial growth by measuring the optical density (Casey J. T. et al., J. Microbiol. Meth [Book], 2004, 58: pages 327-334; Patton T et al., J. Microbiol. Meth [Book], 2006, 64: pages 84-95).

96-well U-shaped sterile microplates with a capacity of 200 µl were used. For each microplate, two control rows were prepared:
  A row containing 200 µl of the MH liquid medium (sterility control and negative control).
  A row containing 150 µl of the MH liquid medium and 50 µl of the bacterial inoculum at $2\times10^7$ CFU/ml (positive control).

For AMX and cineole, two rows were prepared containing 100 µl of MH liquid medium, 50 µl of the bacteria inoculum at $2\times10^7$ CFU/ml and 50 µl of decreasing concentrations of antimicrobial agents. The AMX concentrations used are: 50-25-12.5-6.25-3.1-1.6-0.8-0.4-0.20-0.10-0.05-0.025 µg/ml. The cineole concentrations used are: 100-50-25-12.5-6.25-3.1-1.6-0.8-0.4-0.20-0.10-0.05 µl/ml. The optical densities (OD) were determined at 540 nm using a microplate spectrophotometer (Versamax, Molecular Devices, USA). The OD was measured at time t=0 and after 22 hours of incubation at 30° C. The percentage of inhibition of the antimicrobial agents with respect to each of the six strains was calculated according to Casey J. T. et al. (J. Microbiol. Meth. [Book], 2004, 58: pages 327-334) according to the following formula:

$$\% \text{ inhibition} = 1 - \frac{OD_{T22} - OD_{T0}}{OD_{C22} - OD_{C0}} \times 100$$

With $OD_{T0}$=OD of the test well at time t=0, $OD_{T22}$=OD of the test well after 22 h of incubation, $OD_{C0}$=OD of the positive control well at time t=0, $OD_{C22}$=OD of the positive control well after 22 h of incubation.

After having determined the PICs of AMX and cineole alone, the antibacterial power of the combination of AMX and cineole was evaluated. The same technique of microplate microdilution was used. The AMX-cineole combinations were prepared in sterile tubes as follows:
  AMX 50% PIC+cineole 40% PIC
  AMX 50% PIC+cineole 30% PIC
  AMX 50% PIC+cineole 20% PIC
  AMX 25% PIC+cineole 40% PIC
  AMX 25% PIC+cineole 30% PIC
  AMX 25% PIC+cineole 20% PIC.

The fractional inhibitory concentration index (FIC-index) expressing the degree of synergism of the AMX-cineole combination was calculated according to the following formula (Odds F. C. et al., J. Antimicrob. Chemoth. [Book], 2003, 52: page 1).

$$\text{FIC-index} = \frac{PIC_{AMX+Cineole}}{PIC_{AMX\ alone}} \frac{PIC_{AMX+Cineole}}{PIC_{Cineole\ alone}}$$

The AMX-cineole combination is considered:
  Synergistic when the FIC-index is ≤0.5
  Additive when 0.5<FIC-index <1
  Indifferent when 1<FIC-index <2
  Antagonistic when FIC-index >2.

Results
Determination of the PICs of Amoxicillin and Cineole

The antibacterial activity of AMX with respect to the three strains of *E. coli* and of the three strains of *K. pneumoniae* is comparable (cf. table 1). The minimum inhibitory concentrations (MIC, minimum concentration making it possible to obtain 100% inhibition) are of the order of 50 µg/ml (p>0.05). Cineole also has a comparable antibacterial activity with respect to the three strains of *E. coli* and three strains of *K. pneumoniae* (cf. table 2). The MICs are of the order of 100 µl/ml (p>0.05).

TABLE 1

| Partial inhibitory concentrations of amoxicillin | | |
|---|---|---|
| Strains | 50% PIC (µg/ml) | 25% PIC (µg/ml) |
| *Escherichia coli* | | |
| P956 | 1.1 ± 0.25 | 0.7 ± 0.14 |
| P933 | 1.3 ± 0.24 | 0.5 ± 0.10 |
| P7847 | 1.5 ± 0.13 | 0.8 ± 0.17 |

TABLE 1-continued

Partial inhibitory concentrations of amoxicillin

| Strains | 50% PIC (µg/ml) | 25% PIC (µg/ml) |
|---|---|---|
| *Klebsiella pneumoniae* | | |
| H1878 | 1.6 ± 0.17 | 0.9 ± 0.09 |
| H2001 | 1.3 ± 0.12 | 0.6 ± 0.14 |
| H1893 | 1.7 ± 0.09 | 0.8 ± 0.12 |

TABLE 2

Partial inhibitory concentrations of cineole

| Strains | 40% PIC (µl/ml) | 30% PIC (µl/ml) | 20% PIC (µl/ml) |
|---|---|---|---|
| *Escherichia coli* | | | |
| P956 | 6.2 ± 0.20 | 2.6 ± 0.12 | 1.2 ± 0.16 |
| P933 | 6.8 ± 0.14 | 2.3 ± 0.09 | 1.3 ± 0.24 |
| P7847 | 6.5 ± 0.10 | 2.7 ± 0.12 | 1.2 ± 0.11 |
| *Klebsiella pneumoniae* | | | |
| H1878 | 7.1 ± 0.12 | 2.9 ± 0.12 | 0.4 ± 0.12 |
| H2001 | 6.9 ± 0.12 | 3.1 ± 0.10 | 0.7 ± 0.09 |
| H1893 | 6.8 ± 0.09 | 2.7 ± 0.09 | 0.6 ± 0.12 |

Evaluation of the Percentages of Inhibition of the Combination of Amoxicillin and Cineole The combination of AMX and cineole gives percentages of inhibition higher than that for the addition of the two (cf. tables 3 and 4). Specifically, the 50% PIC of AMX (1.1-1.7 µg/ml) combined with the 40% PIC of cineole (6.2-7.1 µl/ml) give 100% inhibition of growth for all the strains tested.

TABLE 3

Percentages of inhibition of the combinations of AMX (50% PIC) with cineole (40% PIC, 30% PIC and 20% PIC)

| Strains | AMX + Cineole 50% PIC + 40% PIC | AMX + Cineole 50% PIC + 30% PIC | AMX + Cineole 50% + PIC 20% PIC |
|---|---|---|---|
| *Escherichia coli* | | | |
| P956 | 100.0 ± 0.0 | 92.5 ± 0.56 | 80.4 ± 0.69 |
| P933 | 100.0 ± 0.0 | 95.2 ± 0.75 | 81.5 ± 0.59 |
| P7847 | 100.0 ± 0.0 | 90.8 ± 1.29 | 79.4 ± 0.47 |
| *Klebsiella pneumoniae* | | | |
| H1878 | 100.0 ± 0.0 | 90.2 ± 0.68 | 82.8 ± 0.94 |
| H2001 | 100.0 ± 0.0 | 93.7 ± 0.80 | 81.2 ± 0.46 |
| H1893 | 100.0 ± 0.0 | 90.5 ± 0.25 | 85.2 ± 0.41 |

TABLE 4

Percentages of inhibition of the combinations of AMX (25% IC) with cineole (40% PIC, 30% PIC and 20% PIC)

| Strains | AMX + Cineole 25% PIC + 40% PIC | AMX + Cineole 25% PIC + 30% PIC | AMX + Cineole 25% PIC + 20% PIC |
|---|---|---|---|
| *Escherichia coli* | | | |
| P956 | 72.0 ± 0.38 | 62.1 ± 0.22 | 55.3 ± 0.75 |
| P933 | 73.1 ± 0.45 | 59.4 ± 0.32 | 51.2 ± 0.48 |
| P7847 | 70.1 ± 0.46 | 63.3 ± 0.36 | 53.4 ± 0.60 |
| *Klebsiella pneumoniae* | | | |
| H1878 | 74.4 ± 0.28 | 61.2 ± 0.26 | 56.3 ± 0.38 |
| H2001 | 72.4 ± 0.25 | 60.2 ± 0.77 | 53.9 ± 0.67 |
| H1893 | 71.1 ± 0.29 | 64.4 ± 0.34 | 52.6 ± 0.35 |

This powerful synergism was confirmed by calculating the fractional indices (FIC-index, cf. table 5) for the MICs of amoxicillin and cineole. For the six bacterial strains tested, they vary between 0.08 and 0.10. These results, less than 0.5, are evidence of strong synergism of action between AMX and cineole.

TABLE 5

FIC-index of the amoxicillin and cineole combination

| | 100% MIC | | | |
|---|---|---|---|---|
| Strains | Alone | Combined | FIC-Index | Result |
| *E. coli* P956 | 50-100 | 1.1-6.2 | 0.08 | Synergism |
| *E. coli* P933 | 50-100 | 1.3-6.8 | 0.09 | Synergism |
| *E. coli* P7847 | 50-100 | 1.5-6.5 | 0.10 | Synergism |
| *K. pneumoniae* 111878 | 50-100 | 1.6-7.1 | 0.10 | Synergism |
| *K. pneumoniae* 112001 | 50-100 | 1.3-6.9 | 0.10 | Synergism |
| *K. pneumoniae* 111893 | 50-100 | 1.7-6.8 | 0.10 | Synergism |

Discussion

The results obtained clearly show that the strains tested, which are highly resistant to AMX, become sensitive at minimum AMX concentrations when AMX is combined with cineole. Thus, 100% inhibition of growth of all the bacterial strains tested was obtained with the AMX-cineole combination (50% IC+40% IC). This combination makes it possible to obtain antibacterial power similar to that of AMX alone or to cineole alone with concentrations largely inferior to the MIC of AMX or of cineole. Specifically, by comparing the concentrations used for 100% inhibition, it is noted that the concentration of AMX used in combination with cineole is 25 times less than that of AMX alone and that of cineole used in combination with MAX is 15 times less than that of cineole alone.

The bactericidal activity of this combination of AMX and cineole results from strong synergistic action, as demonstrated by the calculation of the fractional index (index of less than or equal to 0.1).

These tests as a whole demonstrate the efficacy of the combination of AMX and cineole against BSBL-resistant bacteria and its value in the fight for holding bacterial resistance at bay.

Example 2—In Vitro Study of the Effect of Cineole on the Inhibition of Amoxicillin by β-Lactamases This study is based on an enzymatic test first placing AMX combined with cineole in contact with ß-lactamases. The antibacterial activity of this antibiotic was then checked on an AMX-sensitive strain of *Escherichia coli*.

Materials and Methods

Biological Materials, Culture Medium and Antimicrobial Agents

An amoxicillin-sensitive bacterial strain of *Escherichia coli* (ATCC 8739) was supplied by the national hygiene institute (INH-Rabat).

For each test performed, precultures of this *E. coli* strain of 24 h at 37° C. were prepared from this bacterial strain (frozen beforehand at −20° C.). From these precultures, bacterial inocula of $3.3 \times 10^6$ CFU/ml were prepared, adjusting the optical density to 540 nm.

The liquid and agar Mueller-Hinton culture media were supplied by BIOKAR (France). The composition of this medium was described previously. The preparation of the two media was performed according to the supplier's instructions.

Disks charged with antibiotics (diameter Ø=6 mm) were used for the enzymatic test in agar medium (AMX: amoxicillin and AMC: amoxicillin+clavulanic acid). They were supplied by the national hygiene institute (INH-Rabat). The AMX used for the enzymatic test in liquid medium was supplied by Sigma Aldrich (France).

The cineole was supplied by Sigma Aldrich (France). Its preparation was performed by emulsifying in 0.2% (v/v) of agar-agar according to the method described by Remmal et al. (J. Essent. Oil. Res. [Book], 1993, 5: pages 1179-1184).

The ß-lactamase powder was supplied by Sigma Aldrich (France). It was dissolved according to the supplier's instructions, at 10 mg/ml in 0.1 M of Tris HCl at pH 7, containing 0.1% of gelatin. The ß-lactamase (0.03 U/ml) thus prepared was stored between 2 and 8° C.

Experimental Protocol in Agar Medium

In agar medium, the infra-inhibitory concentration of cineole (the highest concentration for which cineole does not induce any inhibition) was determined via the microdilution method described previously. It is of the order of 0.002 µl/ml.

Starting with a 24 h sensitive preculture of *E. coli*, eighteen Petri dishes of the agar MH medium were inoculated by surface plating. Six control dishes and two test dishes were prepared as follows:

Dishes 1 and 2 correspond to the controls of sensitivity of the strain to the antibiotics:

Control 1: Three disks charged with AMX alone at 20 µg/ml were deposited aseptically onto the surface of dish no 1.

Control 2: Three disks charged with AMC alone at 30 µg/ml were deposited aseptically onto the surface of dish no 2.

Dishes 3 and 4 correspond to the controls of the β-lactamase activity on the antibiotics:

Control 3: Three disks charged with AMX at 20 µg/ml were deposited aseptically onto the surface of dish no 3. 10 µl of β-lactamase at 0.03 U/ml were added to the surface of each of these three disks.

Control 4: Three disks charged with AMC at 30 µg/ml were deposited aseptically onto the surface of dish no 4. 10 µl of β-lactamase at 0.03 U/ml were added to the surface of each of these three disks.

Dishes 5 and 6 correspond to the controls of the antibacterial activity of the antibiotics combined with cineole (infra-inhibitory concentration):

Control 5: Three disks charged with AMX at 20 µg/ml were deposited aseptically onto the surface of dish no 5. 10 µl of cineole at 0.002 µl/ml were added to the surface of each of these three disks.

Control 6: Three disks charged with AMC at 30 µg/ml were deposited aseptically onto the surface of dish no 6. 10 µl of cineole at 0.002 µl/ml were added to the surface of each of these three disks.

Dishes 7 and 8 correspond to the tests of the effect of cineole on amoxicillin inhibition by the β-lactamases:

Test 1: Three disks charged with AMX at 20 µg/ml were deposited aseptically onto the surface of dish no 7. 10 µl of β-lactamase at 0.03 U/ml and 10 µl of cineole at 0.002 µl/ml were added to the surface of each of these three disks.

Test 2: Three disks charged with AMC at 30 µg/ml were deposited aseptically onto the surface of dish no 8. 10 µl of β-lactamase at 0.03 U/ml and 10 µl of cineole at 0.002 µl/ml were added to the surface of each of these three disks.

After incubation of the eight Petri dishes for 18 h at 37° C., the diameters of the inhibition halos were measured.

Experimental Protocol in Liquid Medium

The MIC of AMX at 100% with respect to the sensitive strain of *Escherichia coli*, determined via the microdilution method described previously, is of the order of 6 µg/ml.

Starting with a 24 h preculture of the sensitive strain of *E. coli*, bacterial inocula at $3.3 \times 10^6$ CFU/ml were prepared, adjusting the optical density to 540 nm.

Five control tubes and one test tube were prepared as described in table 6 (cf. below).

Tube no 1 corresponds to the sterility control of the medium. Tube no 2 corresponds to the positive control of viability of the bacterial strain. Tube no 3 corresponds to the control of sensitivity of the strain to AMX. Tube no 4 corresponds to the control of non-inhibition of bacterial growth with an infra-inhibitory concentration of cineole. Tube no 5 corresponds to the control of degradation of AMX in the presence of ß-lactamase. Tube no 6 corresponds to the test of the effect of cineole on amoxicillin inhibition by the β-lactamases.

TABLE 6

Content of the control and test tubes for the study in liquid medium

| Tubes | MH liquid medium | Bacterial inoculum ($3.3 \times 10^6$ CFU/ml) | AMX (6 µg/ml) | Cineole (0.002 µl/ml) | β-lactamase (0.03 U/ml) |
|---|---|---|---|---|---|
| Tube No. 1: | 1000 µl | — | — | — | — |
| Tube No. 2: | 970 µl | 30 µl | — | — | — |
| Tube No. 3: | 940 µl | 30 µl | 30 µl | — | — |
| Tube No. 4: | 940 µl | 30 µl | — | 30 µl | — |
| Tube No. 5: | 930 µl | 30 µl | 30 µl | — | 10 µl |
| Tube No. 6: | 900 µl | 30 µl | 30 µl | 30 µl | 10 µl |

The OD was measured at time t=0, and after 22 hours of incubation at 30° C. The percentage of inhibition was then calculated according to the formula described previously:

$$\% \text{ inhibition} = 1 - \frac{OD_{T22} - OD_{T0}}{OD_{C22} - OD_{C0}} \times 100$$

With $OD_{T0}$=OD of the test tube at time t=0, $OD_{T22}$=OD of the test tube after 22 h of incubation, $OD_{C0}$=OD of the positive control tube at time t=0, $OD_{C22}$=OD of the positive control tube after 22 h of incubation.

Results
In Agar Medium (Cf. Table 7 Below)

TABLE 7

Diameters of the sensitive *Escherichia coli* inhibition halos (in mm)

| Treatment | Diameters of the halos (mm) * |
|---|---|
| Control 1: AMX alone | 15 ± 1.0 |
| Control 2: AMC alone | 16 ± 0.4 |
| Control 3: AMX + β-lactamase | 6 ± 0.0 |
| Control 4: AMC + β-lactamase | 13 ± 0.5 |
| Control 5: AMX + cineole | 17 ± 0.3 |
| Control 6: AMC + cineole | 18 ± 0.9 |
| Test 1: AMX + β-lactamase + cineole | 12 ± 1.0 |
| Test 2: AMC + β-lactamase + cineole | 15 ± 0.9 |

* Mean of three inhibition halo values

The measurements of the inhibition halo diameters show that:
The strain of *E. coli* used is indeed sensitive to AMX (20 μg) and to the combination of AMX and clavulanic acid (AMC 30 μg) with halo diameters of 15 and 16 mm, respectively.
The addition of cineole at an infra-inhibitory concentration (0.002 μl/ml) slightly increases the size of the inhibition halos, to 17 mm for AMX (20 μg) and to 18 mm for AMC (30 μg).
The addition of ß-lactamases (0.03 U/ml) eliminates the AMX inhibition halo (20 μg) (6 mm being the diameter of the disk) and reduces the AMC inhibition halo (30 μg) to about 13 mm.
The addition of ß-lactamases (0.03 U/ml) and cineole (0.002 μl/ml) considerably reduces the inhibition induced with the ß-lactamases, with halo diameters of the order of 12 mm for AMX (20 μg) and 15 mm for AMC (30 μg).

In Liquid Medium (Cf. Table 8 Below)

TABLE 8

Percentage of inhibition of growth of the sensitive strain of *Escherichia coli*

| Treatment | % inhibition |
|---|---|
| Control 4: Cineole alone | 0% ± 0.0 |
| Control 3: AMX alone | 100% ± 0.0 |
| Control 5: AMX + β-lactamase | 0% ± 0.0 |
| Test 1: AMX + β-lactamase + cineole | 83.4% ± 1.1 |

Table 8 shows that:
The cineole concentration used (0.002 μl/ml) is indeed infra-inhibitory, there was no growth inhibition (control 4).
In the presence of ß-lactamases (0.03 U/ml), the percentage of inhibition of growth of the sensitive strain with AMX (6 μg/ml) is zero (control 5).
In the presence of ß-lactamase (0.03 U/ml) and cineole (0.002 μl/ml), the percentage of inhibition of growth of the sensitive strain with AMX (6 μg/ml) is of the order of 83.4% (test 1).

Discussion
The study performed in agar medium made it possible to show that:
In the presence of cineole, at an infra-inhibitory concentration, the antibacterial activity of AMX and of AMC was improved (inhibition halo diameters greater than those obtained with the antibiotics alone). Thus, the activity of AMX and of AMC are increased in the presence of cineole (at infra-inhibitory concentrations).
In the presence of ß-lactamases, the inhibition induced with AMX (20 μg) was zero and that induced with AMC (30 μg) was largely reduced. This is due to hydrolysis of the ß-lactam ring of amoxicillin. The ß-lactamase is only partially inhibited with clavulanic acid.
In the presence of ß-lactamases and cineole, the antibacterial activity of AMX and of AMC was increased (inhibition halo diameters obtained comparable to those obtained with the antibiotics alone). Insofar as cineole was used at an infra-inhibitory concentration, the increase in antibacterial activity might be explained by a reduced efficacy of the β-lactamases on amoxicillin in the presence of cineole.

The study performed in liquid medium made it possible to show that:
In the presence of ß-lactamase, AMX totally loses its antibacterial activity, which proves the total degradation of this antibiotic by hydrolysis of the ß-lactam ring.
In the presence of ß-lactamases and cineole, the percentage of AMX inhibition is of the order of 83.4%. These results show that in the presence of cineole at an infra-inhibitory concentration, AMX acquires protection against ß-lactamase which no longer manages to maintain its activity. The antibacterial activity of AMX is thus preserved.

These results as a whole show that amoxicillin combined with cineole is only sparingly sensitive to ß-lactamases. Without being bound by this theory, this might be due to complexation of the amoxicillin molecules in the presence of cineole, which prevents the β-lactamases from attacking the β-lactam ring of AMX.

Example 3—Study of the Antibacterial Activity of Rabbit Serum Treated with a Combination of Amoxicillin, Clavulanic Acid and Cineole Materials and Methods
Biological Materials, Culture Medium and Antimicrobial Agents A multi-resistant BSBL bacterial strain of *Escherichia coli* was supplied by the national hygiene institute (INH-Rabat). 24 h precultures at 37° C. were prepared using the bacterial strain (frozen beforehand at −20° C.). Using these precultures, bacterial inocula of $2 \times 10^7$ CFU/ml were prepared, adjusting the optical density to 540 nm.

The liquid and agar Mueller-Hinton (MH) media were supplied by BIOKAR (France). The composition of these media was described previously. The preparation of the two media was performed according to the supplier's instructions.

The six rabbits used in this study are female rabbits of New Zealand race, supplied by a specialist breeder. They are 70 to 75 days old and weigh about 2 kg. They were divided randomly into two batches of three rabbits and were fed ad libitum with an industrial feed of fattening type.

Experimental Protocol
The rabbits of the first batch received a single dose of AMC comprising 1.5 g of amoxicillin and 186.5 mg of clavulanic acid. The rabbits of the second batch received a single dose of AMC combined with cineole comprising 1.5 g of amoxicillin, 186.5 g of clavulanic acid and 300 mg of cineole.

The solutions of the two treatments, reconstituted with purified water, were administered to the rabbits by enteral tube feeding.

After administration of the treatment, the rabbits were immobilized by restraint using a suitable device. Their ears were exposed to an infrared lamp so as to dilate the marginal and central auricular veins. 0.5 ml blood samples were then taken from the central auricular vein at time T=0 ($T_0$) (before the administration), at time $T_1$ (after one hour), at time $T_2$ (after two hours), at time $T_3$ (after three hours) and at time $T_6$ (after six hours).

The microdilution method described previously was used to determine the percentage of inhibition of the serum samples.

96-well U-shaped sterile microplates with a capacity of 200 µl were used. The negative control consists of 200 µl of liquid MH medium and the positive control of 150 µl of liquid MH medium and 50 µl of bacterial inoculum at $2\times10^7$ CFU/ml. For each sample of serum collected at a given time, two wells were prepared each containing 100 µl of the liquid MH medium, 50 µl of the bacterial inoculum at $2\times10^7$ CFU/ml and 50 µl of serum.

For each sample, an OD reading is taken at t=0 and after incubation of the microplates for 22 hours at 30° C. The percentage of inhibition of the various serum samples was calculated according to the formula described previously:

$$\% \text{ inhibition} = 1 - \frac{OD_{T22} - OD_{T0}}{OD_{C22} - OD_{C0}} \times 100$$

With $OD_{T0}$=OD of the test well at time t=0, $OD_{T22}$=OD of the test well after 22 h of incubation, $OD_{C0}$=OD of the positive control well at time t=0, $OD_{C22}$=OD of the positive control well after 22 h of incubation.

Results

Figure 1:
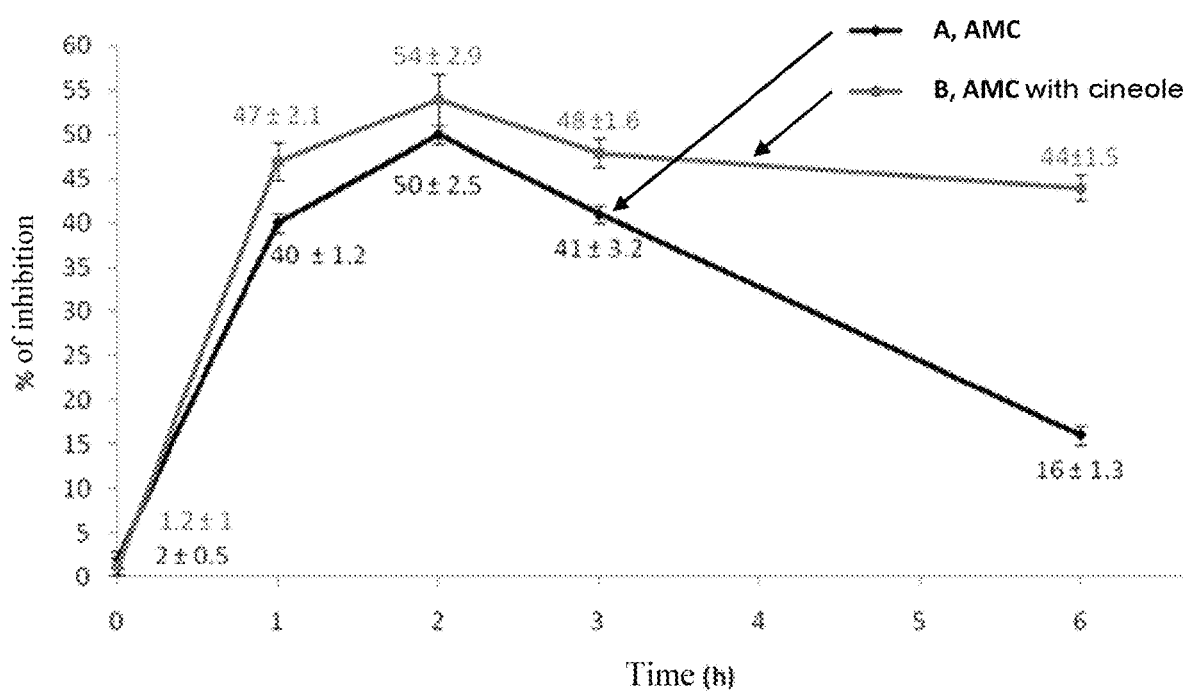
FIG. 1: Study of the antibacterial activity of rabbit serum treated with a combination of amoxicillin, clavulanic acid and cineole. A (AMC without cineole): after oral administration of a single dose of a composition comprising amoxicillin (1.5 g) and clavulanic acid (186.5 mg) to 3 rabbits, the percentage of serum inhibition at times $T_0$, $T_{1h}$, $T_{2h}$, $T_{3h}$ and $T_{6h}$ was calculated with respect to a BSBL multi-resistant strain of *Escherichia coli*. B (AMC with cineole): after oral administration of a single dose of a composition comprising amoxicillin (1.5 g), clavulanic acid (186.5 mg) and cineole (300 mg) to 3 rabbits, the percentage of serum inhibition at times $T_0$, $T_{1h}$, $T_{2h}$, $T_{3h}$ and $T_{6h}$ was calculated with respect to a BSBL multi-resistant strain of *Escherichia coli*.

FIG. 1 shows the monitoring of the percentages of inhibition of bacterial growth by the serum samples from rabbits of the batch treated with AMC alone (amoxicillin/clavulanic acid combination) and of the batch treated with AMC boosted with cineole over time.

Before administration of the treatment (time $T_0$), the antibacterial activity of the serum samples from rabbits of the two is virtually zero. One hour after administration of the treatment ($T_1$), the inhibition induced with the serum from the rabbits treated with AMC alone is of the order of 40±1.2%, whereas that induced with the serum from rabbits treated with AMC and cineole is of the order of 47±2.1%. After two hours of treatment, the percentages of inhibition are 50±2.5% for the sera from rabbits treated with AMC alone and 54±2.9% for those treated with AMC boosted with cineole. After three hours of treatment, the percentages of inhibition fall to 41±3.2% for the rabbits treated with AMC alone and to 48±1.6% for the rabbits treated with AMC boosted with cineole. Finally, after six hours of treatment, the percentages of inhibition drop to 16±1.3% for the sera from rabbits treated with AMC alone, whereas they are still of the order of 44±1.5% for the rabbits treated with AMC boosted with cineole.

Thus, the percentages of inhibition obtained with the serum samples from the rabbits of the first batch treated with the combination of amoxicillin, clavulanic acid and cineole are significantly higher than those obtained with the serum samples from the rabbits of the reference batch treated with the combination of amoxicillin and clavulanic acid (p<0.05).

Example 4—Galenical Development of a Formulation Comprising Amoxicillin, Clavulanic Acid and Cineole Materials and Methods All the starting materials, active principles and excipients used are of pharmaceutical grade.

This formulation is characterized by the presence of cineole, which is a volatile active principle. To stabilize this volatile compound, several excipients or combinations of excipients having adsorbent properties were tested (cf. table 9 below).

The process tested for form 8 (groundnut oil) consists in introducing a step of wetting the granule obtained with the mixture of the other active principles, amoxicillin and clavulanic acid, and of the excipients with an oily phase comprising cineole. The wetting step may be followed by a step of lubrication, mixing and screening.

TABLE 9

Composition of adsorbents in the test formulations

| Adsorbents | Test formulations |  |  |  |  |  |  |  |
|---|---|---|---|---|---|---|---|---|
|  | Form 1 | Form 2 | Form 3 | Form 4 | Form 5 | Form 6 | Form 7 | Form 8 |
| Levillite | ✓ |  | ✓ | ✓ |  |  |  |  |
| Tixosil |  | ✓ |  | ✓ |  |  |  |  |
| Talc |  |  | ✓ |  |  |  |  |  |
| Aerosil |  |  | ✓ | ✓ |  |  |  |  |
| Dimethicone |  |  |  |  | ✓ |  |  |  |
| syloid |  |  |  |  |  |  |  |  |
| Syloid |  |  |  |  |  | ✓ |  |  |
| Starcap |  |  |  |  |  |  | ✓ |  |
| Groundnut oil |  |  |  |  |  |  |  | ✓ |

All the starting materials were screened before mixing on various grates of a FREWITT screening mesh.

Mixing of the starting materials was performed in a HOBART mixer.

Bagging was performed using a MARCHESINI bagging machine.

The temperature and the relative humidity of the manufacturing room were, respectively, of the order of <20° C. and <15%.

The wetting solution, made for the cineole stabilization process, was prepared in a closed chamber to avoid any evaporation.

For each test form, a full quality control including the dosage of the three active principles (amoxicillin, clavulanic acid and cineole) was performed:
- on the final mixture, at the end of manufacture (ten sampling points) at time $T_0$ and after 24 h, 48 h and 72 h of exposure at a temperature <20° C. and for an ambient humidity <15%;
- on the bag at the end of filling (ten sampling points).

Contents of active principles (%) between 95% and 105% are judged to be compliant. The homogeneity of the mixture was checked by calculating the coefficients of variation (CV %) of the individual contents obtained for the ten sampling points. Coefficients of variation of less than or equal to 2% are judged to be compliant.

Results

The mean contents of amoxicillin and clavulanic acid are compliant for all the test forms (forms 1 to 8). As regards cineole (cf. table 10 below), forms 1 to 7 show, from the final mixing, a cineole content less than 95%, this content decreasing further substantially after 24 h, 48 h and 72 h of exposure at a temperature <20° C. and for an ambient humidity <15%.

Form 8 (groundnut oil) makes it possible, however, to stabilize cineole. Specifically, the cineole content present in this form is between 95% and 105% in the final mixture and is maintained in this range after 24 h, 48 h and 72 h of exposure at a temperature <20° C. and for an ambient humidity <15%.

The homogeneity of the final mixture and of the bagging is also compliant for formula 8, the values for the coefficients of variation (CV %) of the contents not exceeding 2%.

TABLE 10

Cineole content (%) as a function of the various adsorbents tested

| Feasibility tests | Cineole content (%)/Coefficient of variation (%) | | | | |
|---|---|---|---|---|---|
| | Final mixture | Bag/end of filling | Stability of the final mixture | | |
| | | | After 24 h | After 48 h | After 72 h |
| Form 1 | 81.9%/0.9% | 69.8%/1.5% | 75.2%/1.7% | 62.2%/0.9% | 57.8%/0.7% |
| Form 2 | 90.9%/1.7% | 75.6%/1.1% | 81.0%/1.5% | 70.4%/1.3% | 62.0%/1.5% |
| Form 3 | 89.0%/0.9% | 72.3%/1.6% | 74.2%/1.3% | 70.1%/1.1% | 59.3%/1.6% |
| Form 4 | 94.1%/0.6% | 92.1%/0.8% | 86.3%/1.3% | 80.7%/1.8% | 72.5%/1.3% |
| Form 5 | 75.9%/1.6% | 72.6%/1.2% | 60.8%/1.0% | 55.7%/1.6% | 50.8%/1.1% |
| Form 6 | 90.9%/1.3% | 86.2%/1.3% | 84.2%/1.5% | 77.2%/1.2% | 70.3%/1.7% |
| Form 7 | 93.9%/0.9% | 91.6%/0.7% | 88.1%/1.6% | 80.3%/1.4% | 74.2%/1.5% |
| Form 8 | 102.3%/0.8% | 102.1%/1.2% | 102.1%/1.0% | 101.8%/1.0% | 101.7%/1.3% |

Moreover, the tests of quantification of impurities of the three active principles (amoxicillin, clavulanic acid and cineole) in the final mixture exposed to a temperature <20° C. and to an ambient humidity <15% for 24 h, 48 h and 72 h are all compliant with the acceptance criteria (results not shown). The results for the other tests of quality of the final mixture and of the distribution in bags are also all compliant with the acceptance criteria (results not shown).

Example 5—Example of Pharmaceutical Formulation According to the Invention

| Name of the component | Amount for a 3 g single-dose bag |
|---|---|
| Amoxicillin trihydrate | Corresponding to an amount of amoxicillin of 500 mg |
| 1:1 mixture of potassium clavulanate and hydrated colloidal silica | Corresponding to an amount of clavulanic acid of 62.5 mg |
| Cineole | 100 mg |
| Syloid® A1 FP | 540 mg |
| Aspartame | 36 mg |
| Groundnut oil | 50 mg |
| Croscarmellose sodium | 300 mg |
| Microcrystalline cellulose Avicel ® PH112 | 1241 mg* |
| Magnesium stearate | 18 mg |
| Flavoring | 90 mg |

*The amount of microcrystalline cellulose is adjusted so that the total weight is 3 g.

This formulation was obtained via the following process:

Step 1: Screening and Premixing

The Avicel PH 112, croscarmellose sodium and Syloid Al are mixed after screening.

Step 2: Compacting 2-1 Amoxicillin

Amoxicillin trihydrate is mixed with a portion of the powder premix obtained in step 1 and then compacted. The granules obtained are then calibrated and then fractionated.

2-2 Clavulanic Acid

Clavulanic acid is mixed with a portion of the powder premix obtained in step 1 and then compacted. The granules obtained are next calibrated, and then fractionated.

Step 3: Granulation 3-1 Preparation of the Wetting Solution (S1)

The wetting solution is obtained by mixing cineole and groundnut oil in a closed container, and then fractionated.

3-2 Wetting

The fractions of the compacted mixture comprising amoxicillin obtained in step 2 are wetted with the fractions of solution Si and then mixed. The fractions of the compacted mixture comprising clavulanic acid obtained in step 2 are added.

3-3 Mixing

The various fractions are combined and mixed.

Step 4: Lubrication

Aspartame and the flavoring composition are mixed after screening. Magnesium stearate is then added.

Step 5: Screening and Final Mixing

The final powder is screened and then mixed for a few minutes.

Step 6: Distribution

The final mixture is distributed in bags.

Step 7: Secondary Packaging in Boxes

Example 6—Study of the Stability of a Pharmaceutical Formulation in Powder Form Comprising Amoxicillin, Clavulanic Acid, Cineole and Groundnut Oil Materials and Methods The stability of the pharmaceutical formulation of example 5 was tested under three different conditions (cf. table 11).

TABLE 11

Experimental conditions of the formulation stability study

| | Temperature | Relative humidity (RH) | Duration of the study |
|---|---|---|---|
| Stability study under condition 1 | 25° C. ± 2° C. | 60% ± 5% | 24 months |
| Stability study under condition 2 | 30° C. ± 2° C. | 65% ± 5% | 12 months |
| Stability study under condition 3 | 40° C. ± 2° C. | 75% ± 5% | 6 months |

Climatic chambers at controlled temperature and relative humidity were used so as to keep the formulations under the chosen conditions.

For condition 1, a quality control was performed every 3 months for the first year and every 6 months for the second year (0, 3, 6, 9, 12, 18 and 24 months).

For conditions 2 and 3, a quality control was performed every 3 months (0, 3, 6, 9 and 12 months, for condition 2, and 0, 3 and 6 months for condition 3).

This quality control concerned:
Controlling the organoleptic qualities, the water content and the pH of the suspension.
The dosage of the three active principles (amoxicillin, clavulanic acid and cineole).
Quantification of the impurities of the three active principles.
A microbiological control.

Results

Under the three conditions, throughout the study, the contents of the three active principles were measured between 95% and 105% (cf. tables 12 to 14 below), demonstrating the stability of the composition.

TABLE 12

Results of the stability study under condition 1

|  | T 0 | T 3 | T 6 | T 9 | T12 | T18 | T24 |
|---|---|---|---|---|---|---|---|
| Content of AMX (%) | 100.6% | 100.4% | 100.3% | 100.3% | 100.1% | 99.7% | 99.4% |
| Content of clavulanic acid (%) | 100.2% | 100.1% | 100.1% | 99.8% | 99.7% | 99.5% | 99.0% |
| Content of cineole (%) | 100.8% | 100.5% | 100.4% | 100.2% | 99.9% | 99.5% | 99.2% |

TABLE 13

Results of the stability study under condition 2

|  | T 0 | T 3 | T 6 | T 9 | T12 |
|---|---|---|---|---|---|
| Content of AMX (%) | 100.6% | 100.2% | 99.9% | 99.6% | 99.2% |
| Content of clavulanic acid (%) | 100.2% | 99.8% | 99.5% | 99.4% | 99.1% |
| Content of cineole (%) | 100.8% | 100.3% | 100.0% | 99.6% | 99.3% |

TABLE 14

Results of the stability study under condition 3

|  | T 0 | T 3 | T 6 |
|---|---|---|---|
| Content of AMX (%) | 100.6% | 100.0% | 99.3% |
| Content of clavulanic acid (%) | 100.2% | 99.6% | 98.9% |
| Content of cineole (%) | 100.8% | 99.7% | 99.0% |

The quantification of the impurities of the three active principles is also compliant with the acceptance criteria for the three conditions (results not shown).

The other parameters controlled (water content, appearance of the powder and of the reconstituted suspension, pH of the reconstituted suspension and microbiological control) are all compliant with the acceptance criteria (results not shown).

Thus, the formulation of the invention conserves its chemical, physical, organoleptic and microbiological properties under the three conditions tested.

Example 7—Pharmacokinetic Study in Man

Experimental Protocol:

48 healthy volunteers were recruited for these experiments.

In a first experiment, the volunteers, divided into two groups of 12, received orally either 12 g of the composition of example 5 (i.e. in total 2 g of amoxicillin, 250 mg of clavulanic acid and 400 mg of cineole), or 12 g of a composition that is identical in all respects but free of cineole. Blood samples were taken every 30 minutes for the first 3 hours, and then every hour up to 6 hours, then at 8 hours, at 10 hours and at 24 hours. The plasma concentration of amoxicillin in the samples collected was assayed by chromatography and the serum amoxicillin kinetics analyzed.

In a second experiment, the volunteers, divided into two groups of 12, all first received the same doses as in the previous experiment, before receiving three times a day for one week maintenance doses of 3 g of the same compositions, i.e. either three times 3 g per day of the composition of example 5 (i.e. for each dosage intake 500 g of amoxicillin, 62.5 mg of clavulanic acid and 100 mg of cineole), or three times 3 g per day of a composition that is identical in all respects but free of cineole. Blood samples were taken every 24 hours (minimum concentration) and also two hours later, at the time of the concentration peak (at t=26 h, 50 h, 72 h, etc.) for 7 days. The plasma concentration of amoxicillin in the collected samples was assayed by chromatography, and the serum amoxicillin kinetics analyzed.

Figure 2:
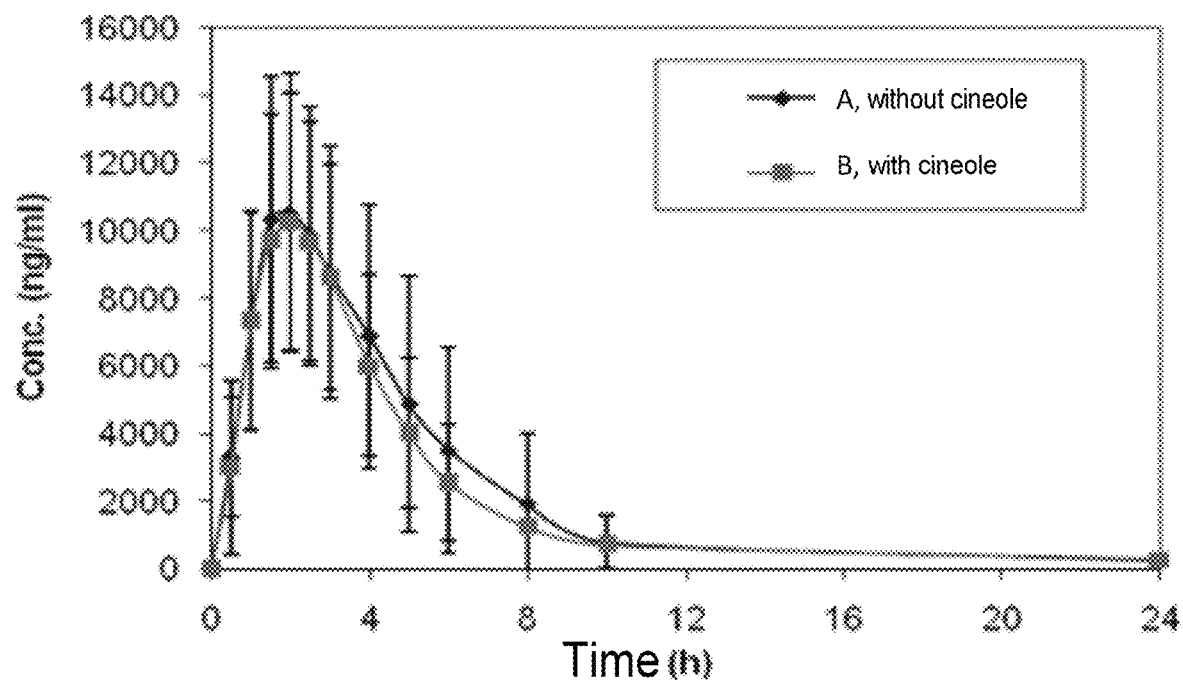
FIG. 2: Monitoring of the mean serum concentrations of amoxicillin for 24 h. A (without cineole): after oral administration of a single dose (12 g) of a composition comprising amoxicillin (2 g) and clavulanic acid (250 mg), the serum concentration of amoxicillin is monitored for 24 h in 12 healthy volunteers. B (with cineole): after oral administration of a single dose (12 g) of a composition comprising amoxicillin (2 g), clavulanic acid (250 mg) and cineole (400 mg), the serum concentration of amoxicillin is monitored for 24 h in 12 healthy volunteers.

Amoxicillin Kinetics for 24 h after Administration of a Single Dose:

The curves for the monitoring of the mean serum concentrations of amoxicillin obtained with volunteers treated with a combination of amoxicillin and clavulanic acid or with a combination of amoxicillin, clavulanic acid and cineole superpose almost perfectly, despite a strong inter-individual variability (cf. FIG. 2). They have the same shape during the absorption phase and the maximum concentrations (Cmax) are reached at about two and a half hours for the two forms. The concentrations begin to decrease at and above two and half hours for the two forms and the two elimination curves remain virtually parallel between the time of administration and 24 h later.

For all the pharmacokinetic parameters studied, namely the area under the curve ($AUC_{0-4}$), the maximum concentration (Cmax), the peak time (Tmax) and the half-life time ($t_{1/2}$), the values obtained are not significantly different between the two conditions tested (cf. table 15 below).

The relative bioavailability of amoxicillin in the form comprising cineole relative to the form not comprising it is:
F (AUC)=0.888.

These results as a whole make it possible to conclude that the two compositions studied have the same bioavailability.

TABLE 15

Pharmacokinetics parameters for serum amoxicillin

| Parameters | AUC$_{0-4}$ (ng · h/ml) | Cmax (ng/ml) | Tmax (hours) | t$_{1/2}$ (hours) |
|---|---|---|---|---|
| Composition of AMX and clavulanic acid | 56161 ± 26760 | 11991 ± 1371 | 2.73 ± 0.68 | 1.66 ± 0.45 |
| Composition of AMX, clavulanic acid and cineole | 50417 ± 12186 | 11322 ± 3171 | 2.38 ± 0.40 | 1.67 ± 0.44 |

Figure 3:
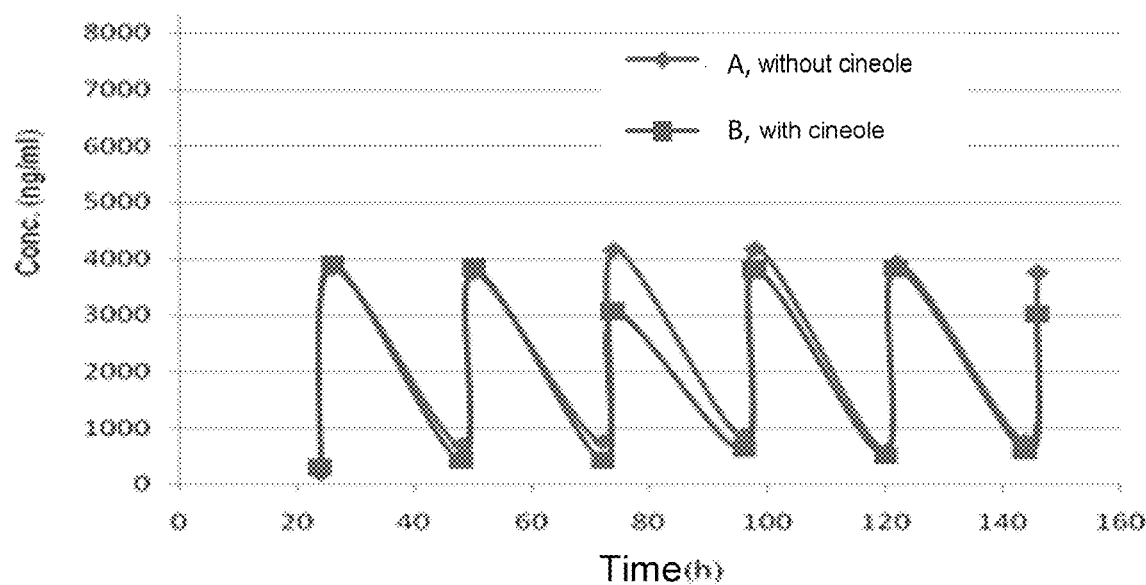
FIG. 3: Monitoring of the mean plasma concentrations of amoxicillin for 7 days. A (without cineole): after oral administration of a single dose (12 g) of a composition comprising amoxicillin (2 g) and clavulanic acid (250 mg), the 12 volunteers receive, 3 times per day for 7 days, maintenance doses (3 g) of the same composition comprising amoxicillin (500 mg) and clavulanic acid (62.5 mg). The plasma concentration of amoxicillin is monitored for 7 days in the 12 healthy volunteers. B (with cineole): after oral administration of a single dose (12 g) of a composition comprising amoxicillin (2 g), clavulanic acid (250 mg) and cineole (400 mg), the 12 volunteers receive, 3 times per day for 7 days, maintenance doses (3 g) of the same composition comprising amoxicillin (500 mg), clavulanic acid (62.5 mg) and cineole (100 mg). The plasma concentration of amoxicillin is monitored for 7 days in the 12 healthy volunteers.

Amoxicillin Kinetics During the Administration of Repeated Doses (7 Days):

The curves for the monitoring of the mean serum concentrations of amoxicillin obtained with volunteers treated with a combination of amoxicillin and clavulanic acid or with a combination of amoxicillin, clavulanic acid and cineole superpose virtually perfectly (cf. FIG. 3).

These results show that the two compositions studied have the same pharmacokinetic behavior during repeated administrations.

Example 8—Clinical Test on Patients with a Sensitive Bacterial Infection

The object of this clinical test was to evaluate, in the case of patients suffering from a urinary infection with amoxicillin-sensitive bacteria, the efficacy of a pharmaceutical formulation comprising amoxicillin, clavulanic acid and cineole relative to a formulation only comprising amoxicillin and clavulanic acid. This randomized clinical test was performed on a population of 28 patients divided into 2 groups (or arms) of 14 patients each. The patients of each group were treated in parallel for 7 days. The patients are men and women over 20 years old.

An antibiogram performed on the patients before the start of the treatment made it possible to confirm that they are all suffering from a urinary infection caused by sensitive bacterial germs.

Efficacy Evaluation Criterion:

The efficacy of the treatments is evaluated by a cytobacteriological examination of the urine (CBEU) performed at the end of the treatment.

Products and Dosage:

Test formulation of example 5 (amoxicillin, clavulanic acid and cineole) comprising 500 mg of amoxicillin, 62.5 mg of clavulanic acid and 100 mg of cineole per 3 grams of powder (corresponding to the content of a bag).

Patient eligible for the treatments of the study received randomly according to the randomization table:
A loading dose of 12 grams (4 bags in one dosage intake) of the test formulation on the first day, then 3 bags per day of the same formulation (one in the morning, one midday and one in the evening) for 6 days (arm A).
A loading dose of 12 grams (4 bags in one dosage intake) of the test formulation on the first day, then 6 bags per day of the same formulation (two in the morning, two at midday and two in the evening) for 6 days (arm B).

Table 16 below summarizes the distribution of the patients in the various arms and also the nature of the bacterial infection detected during the CBEU prior to the treatment.

Results:

The treatment was efficient in all the cases (elimination of the bacterium initially detected) except for one patient in whom the treatment was ineffective in arm A (patient No. 2).

The treatment even proved to be effective in the case of certain patients considered as more complex since they are reputed to be difficult to sterilize in the case of infection, namely patients exhibiting benign hypertrophy of the prostate, diabetic patients, patients exhibiting urethral stenosis, urinary diversions, bladder stones or bladder tumors.

In conclusion, the treatment tested (amoxicillin, clavulanic acid and cineole), just like the reference treatment (amoxicillin, and clavulanic acid), makes it possible efficiently to treat urinary infections caused by sensitive bacterial germs, including those on difficult terrains.

TABLE 16

Characteristics of the patients and their distribution

| No. of the patient | Age (years) | Sex | Bacterium responsible for the patient's urinary infection | Arm |
|---|---|---|---|---|
| 1 | 65 | Male | E. coli | B3 |
| 2 | 44 | Male | E. coli | A5 |
| 3 | 80 | Male | E. coli | A1 |
| 4 | 75 | Female | Staphylococus heamolyticus | B12 |
| 5 | 20 | Male | Staphylococus epidermidis | A14 |
| 6 | 66 | Female | E. coli | A8 |
| 7 | 43 | Female | E. coli | A7 |
| 8 | 46 | Male | Proteus mirabilis | A4 |
| 9 | 66 | Male | Klebsiella pneumoniae | B2 |
| 10 | 69 | Male | Staphylococus agalactiae | A6 |
| 11 | 46 | Male | E. coli | A9 |
| 12 | 58 | Male | Staphylococus agalactiae | A2 |
| 13 | 52 | Male | Staphylococus agalactiae | B9 |
| 14 | 78 | Female | E. coli | B6 |
| 15 | 77 | Female | E. coli | A3 |
| 16 | 69 | Male | Streptococus agalpactie | B4 |
| 17 | 76 | Male | E. coli | B1 |
| 18 | 54 | Female | E. coli | B5 |
| 19 | 55 | Female | Klebsiella oxytoca | B7 |
| 20 | 52 | Female | E. coli | A10 |
| 21 | 74 | Male | E. coli | B8 |
| 22 | 70 | Male | Enterocoque | B10 |
| 23 | 40 | Female | Streptococcus agalactiae | A11 |
| 24 | 85 | Male | Klebsiella pneumoniae | A12 |
| 25 | 26 | Male | E. coli | B11 |
| 26 | 33 | Female | E. coli | A13 |
| 27 | 60 | Male | E. coli | B14 |
| 28 | 90 | Male | Streptocoque D | B13 |

Example 9—Clinical Test on Patients with a Resistant Bacterial Infection

The object of this clinical test was to evaluate, in the case of patients suffering from a urinary infection caused by bacteria that are resistant to a combination of amoxicillin and clavulanic acid, the efficacy of a pharmaceutical formulation comprising amoxicillin, clavulanic acid and cineole. This clinical test was performed on a population of 23 patients treated for 7 days.

The formulation tested (cf. example 2) is a powder comprising 500 mg of amoxicillin, 62.5 mg of clavulanic acid and 100 mg of cineole per 3 grams of powder (corresponding to the contents of one bag).

Each patient first received a loading dose of 12 grams (4 bags in one dosage intake) of the test formulation on the first day, then 6 bags per day of the same formulation (two in the morning, two at midday and two in the evening) for 6 days.

Table 17 below summarizes the characteristics of the patients of this test, including the nature of the bacterial infection detected during the CBEU prior to the treatment.

Results:

The treatment was effective in all the cases (elimination of the bacterium initially detected) except for one patient (patient No. 6).

The case of patient No. 22 is particularly interesting. Specifically, this patient exhibited a urinary infection considered as refractory to all the available antibiotics tested for almost 20 years, including amoxicillin and clavulanic acid, and was cured with the formulation according to the invention.

In conclusion, the formulation according to the invention comprising amoxicillin, clavulanic acid and cineole proved to be very effective against urinary infections caused by bacteria that are resistant to the reference treatment, namely a formulation comprising amoxicillin and clavulanic acid.

TABLE 17

Characteristics of the patients

| No. of the patent | Age | Sex | Bacterium responsible for the patient's urinary infection |
|---|---|---|---|
| 1 | 37 | Female | *Staphylococcus aureus* |
| 2 | 49 | Male | *Pseudomonas aeruginosa* |
| 3 | 46 | Male | *E. coli* |
| 4 | 22 | Female | *E. coli* + *Candida albicans* |
| 5 | 82 | Male | *E. coli* |
| 6 | 37 | Male | *E. coli* |
| 7 | 46 | Male | *Acinetobacter iwoffii* |
| 8 | 83 | Female | *E. coli* |
| 9 | 71 | Male | *E. coli* |
| 10 | 76 | Male | *Klebsiella pneumoniae* |
| 11 | 76 | Male | *E. coli* |
| 12 | 53 | Male | *Klebsiella pneumoniae* |
| 13 | 66 | Female | *E. coli* |
| 14 | 39 | Female | *E. coli* |
| 15 | 84 | Male | *E. coli* |
| 16 | 69 | Male | *Klebsiella pneumoniae* |
| 17 | 77 | Male | *Enterobacter cloacae* |
| 18 | 59 | Male | *Klebsiella pneumoniae* |
| 19 | 21 | Male | *E. coli* |
| 20 | 25 | Female | *E. coli* |
| 21 | 71 | Male | *E. coli* |
| 22 | 65 | Female | *Klebsiella oxytoca* |
| 23 | 49 | Female | *Proteus mirabilis* |

Example 10—Spectroscopic Study of the Formation of Amoxicillin Complexes

The spectroscopy analyses were performed with solutions comprising 500 mg of amoxicillin and, where appropriate, 62.5 mg of clavulanic acid or 100 mg of cineole dissolved in 100 ml of water.

Analysis by mass spectroscopy of amoxicillin dissolved in water (cf. FIG. 4-A) shows the presence of a main peak corresponding to molecular amoxicillin (peak at 349.06 amu) and also another peak corresponding to amoxicillin in dimeric form (peak at 731.17 amu). The amplitude of the peak for the amoxicillin dimers is very largely inferior to that for the peak of molecular amoxicillin. Thus, when it is alone in solution, amoxicillin is very predominantly in molecular form.

When amoxicillin is dissolved in the presence of cineole, in addition to the peaks already observed for amoxicillin alone, new peaks appear in mass spectroscopy (cf. FIG. 4-B). These peaks corresponding to amoxicillin trimers (peak at 1134.24 amu) and to amoxicillin tetramers (peak at 1499.34 amu).

However, when amoxicillin is dissolved in the presence of clavulanic acid, and in the absence of cineole, the spectroscopic profile of amoxicillin is unchanged (results not shown).

Thus, the addition of cineole allows the rearrangement of the amoxicillin molecules in solution in the form of oligomers of 3 to 4 amoxicillin molecules. This rearrangement is not observed when amoxicillin is only in the presence of clavulanic acid.

The invention claimed is:

1. A pharmaceutical formulation in powder form comprising cineole, amoxicillin, and groundnut oil, wherein the formulation comprises a cineole/groundnut oil mass ratio of between 0.1 and 5 and wherein the formulation does not comprise a detergent.

2. The formulation according to claim 1, wherein said formulation also comprises a β-lactamase inhibitor.

3. The formulation according to claim 1, wherein said formulation comprises between about 5 mg and about 100 mg of cineole per gram of powder.

4. The formulation according to claim 1, wherein said formulation comprises between about 20 mg and about 500 mg of amoxicillin per gram of powder.

5. The formulation according to claim 1, wherein said formulation comprises between about 2 mg and about 50 mg of groundnut oil per gram of powder.

6. The formulation according to claim 2, wherein said β-lactamase inhibitor is clavulanic acid and said formulation comprises between about 1 mg and about 100 mg of clavulanic acid per gram of powder.

7. The formulation according to claim 1, wherein the amoxicillin/cineole mass ratio is between 2 and 8.

8. The formulation according to claim 1, wherein the amoxicillin/groundnut oil mass ratio is between 5 and 15.

9. The formulation according to claim 2, wherein the amoxicillin/β-lactamase inhibitor mass ratio is between 5 and 11.

10. The formulation according to claim 1, wherein said formulation also comprises at least one pharmaceutically acceptable excipient or support.

11. The formulation according to claim 2, said formulation comprising groundnut oil, cineole, amoxicillin, and clavulanic acid.

12. The formulation according to claim 1, wherein the cineole/groundnut oil mass ratio is about 2.

13. A method of treating a bacterial infection in an individual comprising the administration of a formulation according to claim 1 to said individual.

14. The method according to claim 13, wherein said bacterial infection is selected from the group consisting of cystitis, recurring acute cystitis, bacterial sinusitis, acute maxillary sinusitis, otitis, acute otitis media, bronchitis, chronic and/or acute bronchitis, bronchopneumopathy, chronic and/or acute bronchopneumopathy, pyelonephritis, upper genital tract infections, parodontitis, severe stomatological infections, abscesses, phlegmons, cellulites, animal bites, bone infections, joint infections, and osteomyelitis.

* * * * *

UNITED STATES PATENT AND TRADEMARK OFFICE
CERTIFICATE OF CORRECTION

PATENT NO. : 11,872,216 B2
APPLICATION NO. : 16/306262
DATED : January 16, 2024
INVENTOR(S) : Adnane Remmal and Ahmed Amine Akhmouch Page 1 of 1

It is certified that error appears in the above-identified patent and that said Letters Patent is hereby corrected as shown below:

In the Specification

Column 14,
Line 52, "than 36 μm." should read --than 36 pm.--.

Column 38,
Lines 31-32, Table 5,
"*K. pneumoniae* 111878
*K. pneumoniae* 112001
*K. pneumoniae* 111893" should read
--*K. pneumoniae* H1878
*K. pneumoniae* H2001
*K. pneumoniae* H1893--.

Column 46,
Line 10, "Solution (51)" should read --Solution (S1)--.
Line 34, "solution Si" should read --solution S1--.

Signed and Sealed this
Sixteenth Day of July, 2024

Katherine Kelly Vidal
*Director of the United States Patent and Trademark Office*